(12) United States Patent
Schmidt et al.

(10) Patent No.: US 7,485,771 B2
(45) Date of Patent: *Feb. 3, 2009

(54) POLYPEPTIDES AND POLYNUCLEOTIDES RELATING TO THE α- AND β-SUBUNITS OF GLUTAMATE DEHYDROGENASES AND METHODS OF USE

(75) Inventors: Robert R. Schmidt, Gainesville, FL (US); Philip Miller, Salem, CT (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 12 days.

This patent is subject to a terminal disclaimer.

(21) Appl. No.: 10/627,886

(22) Filed: Jul. 24, 2003

(65) Prior Publication Data

US 2004/0128710 A1     Jul. 1, 2004

Related U.S. Application Data

(60) Continuation of application No. 09/070,844, filed on May 1, 1998, now abandoned, which is a division of application No. 08/725,596, filed on Oct. 3, 1996, now abandoned, which is a continuation-in-part of application No. 08/541,033, filed on Oct. 6, 1995, now Pat. No. 5,879,941.

(51) Int. Cl.
    *A01H 5/00*     (2006.01)
    *C12N 15/82*     (2006.01)
(52) U.S. Cl. ..................... 800/278; 800/287; 800/298
(58) Field of Classification Search .................. None
See application file for complete search history.

(56) References Cited

U.S. PATENT DOCUMENTS

| | | | | |
|---|---|---|---|---|
| 5,879,941 A | * | 3/1999 | Schmidt et al. | 435/419 |
| 5,998,700 A | * | 12/1999 | Lightfoot et al. | 800/278 |
| 6,084,153 A | * | 7/2000 | Good et al. | 800/290 |
| 6,329,573 B1 | * | 12/2001 | Lightfoot et al. | 800/300.1 |

FOREIGN PATENT DOCUMENTS

WO     WO 9509911     4/1995

OTHER PUBLICATIONS

Oliveira et al, 1997, Plant Physiol. Biochem. 35:185-198.*
Chavez et al, 1995, Plant Mol. Biol. 28:173-188.*
Long et al, 1994, Plant Physiol. 105:115.*
Gupta et al, 1982, Mol. Gen. Genet. 188:378-383.*
Cock, J.M. et al. (1991) "A nuclear gene with many introns encoding ammonium-inducible chloroplastic NADP-specific glutamate dehydrogenase(s) in *Chlorella sorokiniana*" Plant Moleclular Biology 17:1023-1044.
Bascomb, N.F. et al. (1987) "Different Rates of Synthesis and Degradation of Two Chloroplastic Ammonium-inducible NADP-Specific Glutamate Dehydrogenase Isoenzymes during Induction and Deinduction of *Chlorella sorokiniana* Cells" Plant Physiol. 83:85-91.
Bascomb, N.F., R. R. Schmidt (1987) "Purification and Partial Kinetic and Physical Characterization of Two Chloroplast-Localized NADP-Specific Glutamate Dehydrogenase Isoenzymes and Their Preferential Accumulation in *Chlorella sorokiniana* Cells Cultured at Low or High Ammonium Levels" Plant Physiol. 83:75-84.
Prunkard, D.E. et al. (1986) "Effect of Different Carbon Sources on the Ammonium Induction of Different Forms of NADP-Specific Glutamate Dehydrogenase in *Chlorella sorokiniana* Cells Cultured in the Light and Dark" Plant Physio. 81:413-422.
Yeung, A.T. et al. (1981) "Purification of an Ammonium-Inducible Glutamate Dehydrogenase and the Use of its Antigen Affinity Column-Purified Antibody in Specific Immunoprecipitation and Immunoadsorption Procedures" Analytical Biochemistry 110:216-228.
Meredith, M.J. et al. (1978) "Physical and Kinetic Properties of the Nicontinamide Adenine Dinucleotide-specific Glutamate Dehydrogenase Purified from *Chlorella sorokiniana*" Plant Physio. 61:967-974.
Srivastava, H.S., R. P. Singh (1987) "Role and Regulation of L-Glutamate Dehydrogenase Activity in Higher Plants" Phytochemistry 26(3):597-610.
Prunkard, D. E. et al. (1986) "Evidence for Chloroplastic Localization of an Ammonium-Inducible Glutamate Dehydrogenase and Synthesis of its Subunit from a Cytosolic Precursor-Protein in *Chlorella sorokiniana*" Plant Physio. 81:349-355.
Wallsgrove, R.M. et al. (1987) "Barley Mutants Lacking Chloroplast Glutamine Synthetase-Biochemical and Genetic Analysis" Plant Physio. 83:155-158.
Miflin, B.J. P. J. Lea (1976) "The Pathway of Nitrogen Assimilation in Plants" Phytochemistry 15.873-885.
"Niotimasmide Adenine Di Nucleotide Glutamate Dehydrogenase Obtain *Cholerella* Cell Buffer Extract Two Stage Chromatography Phosphate Buffer Elution" (1982) Biochem. Inst., abstract only.
Napoli et al. Introduction of a chimeric chalcone synthase gene into petunia results lin reversible co-suppression of homologous genes in trans. The Plant Cell. 2:279-289 (1990).
Bascomb, N.F. et al. (1985) "Specific Polysome Immunoadsorption to Purify an Ammonium-Inducible Glutamate Dehydrogenase MRNA from *Chlorella sorokiniana* and synthesis of Full Length Double-Stranded cDNA from the Purified MRNA" Plant Physio. 81:527-532.

(Continued)

*Primary Examiner*—Anne R Kubelik
(74) *Attorney, Agent, or Firm*—Saliwanchik, Lloyd & Saliwanchik

(57) ABSTRACT

Amino acid and nucleotide sequences relating to the glutamate dehydrogenase (GDH) enzyme are described. The GDH enzymes described herein were discovered in the alga *Chlorella sorokiniana* in the form of seven different inducible isoenzymes. These isoenzymes are found in the algae as chloroplast-localized hexamers composed of alpha- and beta-subunits. Plants transformed with nucleotide sequences encoding the alpha- or beta-subunits of the enzyme show improved properties, for example, increased growth and improved stress tolerance. A heterohexamer having both α- and β-subunits can have higher aminating:deaminating activity ratio than α-homohexamers or β-homohexamers.

6 Claims, 2 Drawing Sheets

OTHER PUBLICATIONS

Miller, P. W. et al. (1994) "Transcription initiation site of a NADP-specific glutamate dehydrogenase gene and potential use of is promoter region to express foreign genes in ammonium-cultured *Chlorella sorokiniana* cells" Journal of Applied Phycology 6:211-223.

Meredith, M. J., R.R. Schmidt (1991) "NAO-Specific glutamate dehydrogenase isoenzyme localized in mitochondria of nitrate-cultured *Chlorella sorokinian* cells" Plant Physio. 10:67-71.

Mehta, R.A. et al., Engineered polyamine accumulation in tomato enhances phytonutrient content, juice quality, and vine life Nature Biotechnology, Jun. 2002, vol. 20, 613-618.

Park, S.M. et al., Elucidation of anaplerotic pathways in *Corynebacterium glutamicum*, Appl. Microbiol Biotechnol, 1997, vol. 47, 430-440.

\* cited by examiner

SEQUENCE LISTING

```
(1) GENERAL INFORMATION:

(iii) NUMBER OF SEQUENCES: 26

(2) INFORMATION FOR SEQ ID NO: 1:

(i) SEQUENCE CHARACTERISTICS:
          (A) LENGTH: 2140 base pairs
          (B) TYPE: nucleic acid
          (C) STRANDEDNESS: double
          (D) TOPOLOGY: linear (ii) MOLECULE TYPE: cDNA (ix) FEATURE:
          (A) NAME/KEY: CDS
          (B) LOCATION: 33..1610

(xi) SEQUENCE DESCRIPTION: SEQ ID NO: 1:

CTCCTTTCTG CTCGCCCTCT CTCCGTCCCG CC ATG CAG ACC GCC CTC GTC GCC        53
                                    Met Gln Thr Ala Leu Val Ala
                                      1               5

AAG CCT ATC GTG GCC GCC CCG CTG GCG GCA CGC CCG CGC TGC CTC GCG       101
Lys Pro Ile Val Ala Ala Pro Leu Ala Ala Arg Pro Arg Cys Leu Ala
        10                  15                  20

CCG TGG CCG TGC GCG TGG GTC CGC TCC GCC AAG CGC GAT GTC CGC GCC       149
Pro Trp Pro Cys Ala Trp Val Arg Ser Ala Lys Arg Asp Val Arg Ala
    25                  30                  35

AAG GCC GTC TCG CTG GAG GAG CAG ATC TCC GCG ATG GAC GCC ACC ACC       197
Lys Ala Val Ser Leu Glu Glu Gln Ile Ser Ala Met Asp Ala Thr Thr
```

-continued

```
                40                  45                  50                  55
GGC GAC TTC ACG GCG CTG CAG AAG GCG GTG AAG CAG ATG GCC ACC AAG           245
Gly Asp Phe Thr Ala Leu Gln Lys Ala Val Lys Gln Met Ala Thr Lys
                    60                  65                  70
GCG GGC ACT GAG GGC CTG GTG CAC GGC ATC AAG AAC CCC GAC GTG CGC           293
Ala Gly Thr Glu Gly Leu Val His Gly Ile Lys Asn Pro Asp Val Arg
            75                  80                  85
CAG CTG CTG ACC GAG ATC TTC ATG AAG GAC CCG GAG CAG CAG GAG TTC           341
Gln Leu Leu Thr Glu Ile Phe Met Lys Asp Pro Glu Gln Gln Glu Phe
                90                  95                 100
ATG CAG GCG GTG CGC GAG GTG GCC GTC TCC CTG CAG CCC GTG TTC GAG           389
Met Gln Ala Val Arg Glu Val Ala Val Ser Leu Gln Pro Val Phe Glu
        105                 110                 115
AAG CGC CCC GAG CTG CTG CCC ATC TTC AAG CAG ATC GTT GAG CCT GAG           437
Lys Arg Pro Glu Leu Leu Pro Ile Phe Lys Gln Ile Val Glu Pro Glu
120                 125                 130                 135
CGC GTG ATC ACC TTC CGC GTG TCC TGG CTG GAC GAC GCC GGC AAC CTG           485
Arg Val Ile Thr Phe Arg Val Ser Trp Leu Asp Asp Ala Gly Asn Leu
                140                 145                 150
CAG GTC AAC CGC GGC TTC CGC GTG CAG TAC TCG TCC GCC ATC GGC CCC           533
Gln Val Asn Arg Gly Phe Arg Val Gln Tyr Ser Ser Ala Ile Gly Pro
            155                 160                 165
TAC AAG GGC GGC CTG CGC TTC CAC CCC TCC GTG AAC CTG TCC ATC ATG           581
Tyr Lys Gly Gly Leu Arg Phe His Pro Ser Val Asn Leu Ser Ile Met
            170                 175                 180
AAG TTC CTT GCC TTT GAG CAG ATC TTC AAG AAC AGC CTG ACC ACC CTG           629
Lys Phe Leu Ala Phe Glu Gln Ile Phe Lys Asn Ser Leu Thr Thr Leu
        185                 190                 195
CCC ATG GGC GGC GGC AAG GGC GGC TCC GAC TTC GAC CCC AAG GGC AAG           677
Pro Met Gly Gly Gly Lys Gly Gly Ser Asp Phe Asp Pro Lys Gly Lys
200                 205                 210                 215
AGC GAC GCG GAG GTG ATG CGC TTC TGC CAG TCC TTC ATG ACC GAG CTG           725
Ser Asp Ala Glu Val Met Arg Phe Cys Gln Ser Phe Met Thr Glu Leu
                220                 225                 230
CAG CGC CAC ATC AGC TAC GTG CAG GAC GTG CCC GCC GGC GAC ATC GGC           773
Gln Arg His Ile Ser Tyr Val Gln Asp Val Pro Ala Gly Asp Ile Gly
            235                 240                 245
GTG GGC GCG CGC GAG ATT GGC TAC CTT TTC GGC CAG TAC AAG CGC ATC           821
Val Gly Ala Arg Glu Ile Gly Tyr Leu Phe Gly Gln Tyr Lys Arg Ile
            250                 255                 260
ACC AAG AAC TAC ACC GGC GTG CTG ACC CCG AAG GGC CAG GAG TAT GGC           869
Thr Lys Asn Tyr Thr Gly Val Leu Thr Pro Lys Gly Gln Glu Tyr Gly
        265                 270                 275
GGC TCC GAG ATC CGC CCC GAG GCC ACC GGC TAC GGC GCC GTG CTG TTT           917
Gly Ser Glu Ile Arg Pro Glu Ala Thr Gly Tyr Gly Ala Val Leu Phe
280                 285                 290                 295
GTG GAG AAC GTG CTG AAG GAC AAG GGC GAG AGC CTC AAG GGC AAG CGC           965
Val Glu Asn Val Leu Lys Asp Lys Gly Glu Ser Leu Lys Gly Lys Arg
                300                 305                 310
TGC CTG GTG TCT GGC GCG GGC AAC GTG GCC CAG TAC TGC GCG GAG CTG          1013
Cys Leu Val Ser Gly Ala Gly Asn Val Ala Gln Tyr Cys Ala Glu Leu
            315                 320                 325
CTG CTG GAG AAG GGC GCC ATC GTG CTG TCG CTG TCC GAC TCC CAG GGC          1061
Leu Leu Glu Lys Gly Ala Ile Val Leu Ser Leu Ser Asp Ser Gln Gly
            330                 335                 340
TAC GTG TAC GAG CCC AAC GGC TTC ACG CGC GAG CAG CTG CAG GCG GTG          1109
Tyr Val Tyr Glu Pro Asn Gly Phe Thr Arg Glu Gln Leu Gln Ala Val
        345                 350                 355
CAG GAC ATG AAG AAG AAG AAC AAC AGC GCC CGC ATC TCC GAG TAC AAG          1157
```

```
Gln Asp Met Lys Lys Lys Asn Asn Ser Ala Arg Ile Ser Glu Tyr Lys
360                 365                 370                 375

AGC GAC ACC GCC GTG TAT GTG GGC GAC CGC CGC AAG CCT TGG GAG CTG       1205
Ser Asp Thr Ala Val Tyr Val Gly Asp Arg Arg Lys Pro Trp Glu Leu
                380                 385                 390

GAC TGC CAG GTG GAC ATC GCC TTC CCC TGC GCC ACC CAG AAC GAG ATC       1253
Asp Cys Gln Val Asp Ile Ala Phe Pro Cys Ala Thr Gln Asn Glu Ile
            395                 400                 405

GAT GAG CAC GAC GCC GAG CTG CTG ATC AAG CAC GGC TGC CAG TAC GTG       1301
Asp Glu His Asp Ala Glu Leu Leu Ile Lys His Gly Cys Gln Tyr Val
        410                 415                 420

GTG GAG GGC GCC AAC ATG CCC TCC ACC AAC GAG GCC ATC CAC AAG TAC       1349
Val Glu Gly Ala Asn Met Pro Ser Thr Asn Glu Ala Ile His Lys Tyr
    425                 430                 435

AAC AAG GCC GGC ATC ATC TAC TGC CCC GGC AAG GCG GCC AAC GCC GGC       1397
Asn Lys Ala Gly Ile Ile Tyr Cys Pro Gly Lys Ala Ala Asn Ala Gly
440                 445                 450                 455

GGC GTG GCG GTC AGC GGC CTG GAG ATG ACC CAG AAC CGC ATG AGC CTG       1445
Gly Val Ala Val Ser Gly Leu Glu Met Thr Gln Asn Arg Met Ser Leu
                460                 465                 470

AAC TGG ACT CGC GAG GAG GTT CGC GAC AAG CTG GAG CGC ATC ATG AAG       1493
Asn Trp Thr Arg Glu Glu Val Arg Asp Lys Leu Glu Arg Ile Met Lys
            475                 480                 485

GAC ATC TAC GAC TCC GCC ATG GGG CCG TCC CGC AGA TAC AAT GTT GAC       1541
Asp Ile Tyr Asp Ser Ala Met Gly Pro Ser Arg Arg Tyr Asn Val Asp
        490                 495                 500

CTG GCT GCG GGC GCC AAC ATC GCG GGC TTC ACC AAG GTG GCT GAT GCC       1589
Leu Ala Ala Gly Ala Asn Ile Ala Gly Phe Thr Lys Val Ala Asp Ala
    505                 510                 515

GTC AAG GCC CAG GGC GCT GTT TAAGCTGCCC AGGCCCAAGC CACGGCTCAC          1640
Val Lys Ala Gln Gly Ala Val
520                 525

CGGCAATCCA ACCCAACCAA CTCAACGGCC AGGACCTTTT CGGAAGCGGC GCCTTTTT       1700

CAGCCAGGGC CCTCACCTGC CCTTTCATAA CCCTGCTATT GCCGCCGTGC CCCTGCAA       1760

CCACCCCAAG AAGAACTAGC GGCACTTGAC TGCATCAGGA CGGCTATTTT TTTCGCGA       1820

CGCGCTCACC CCGAGAGCCT CTCTCCCCCG AGCCCTAAGC GCTGACGTCC GCCCGACT       1880

GCCTCGCACA TCGCTCGGTT TTGACCCCCT CCAGTCTACC CACCCTGTTG TGAAGCCT       1940

CAGCTCAATT GCCTTTTAGT GTATGTGCGC CCCCTCCTGC CCCCGAATTT TCCTGCCA       2000

AGACGTGCGG TTCCTAGCCT GGTGACCCCA AGTAGCAGTT AGTGTGCGTG CCTTGCCC       2060

CGCTGCCCGG GATGCGATAC TGTGACCTGA GAGTGCTTGT GTAAACACGA CGAGTCAA       2120

AAAAAAAAA AAAAAAAAA                                                   2140

(2) INFORMATION FOR SEQ ID NO: 2:

(i) SEQUENCE CHARACTERISTICS:
        (A) LENGTH: 526 amino acids
        (B) TYPE: amino acid
        (D) TOPOLOGY: linear (ii) MOLECULE TYPE: protein (xi) SEQUENCE DESCRIPTION: SEQ ID NO: 2:

Met Gln Thr Ala Leu Val Ala Lys Pro Ile Val Ala Ala Pro Leu Ala
 1               5                  10                  15

Ala Arg Pro Arg Cys Leu Ala Pro Trp Pro Cys Ala Trp Val Arg Ser
            20                  25                  30
```

-continued

```
Ala Lys Arg Asp Val Arg Ala Lys Ala Val Ser Leu Glu Glu Gln Ile
         35                  40                  45

Ser Ala Met Asp Ala Thr Thr Gly Asp Phe Thr Ala Leu Gln Lys Ala
         50                  55                  60

Val Lys Gln Met Ala Thr Lys Ala Gly Thr Gly Leu Val His Gly
 65                  70                  75                  80

Ile Lys Asn Pro Asp Val Arg Gln Leu Leu Thr Glu Ile Phe Met Lys
                 85                  90                  95

Asp Pro Glu Gln Gln Glu Phe Met Gln Ala Val Arg Glu Val Ala Val
            100                 105                 110

Ser Leu Gln Pro Val Phe Glu Lys Arg Pro Glu Leu Leu Pro Ile Phe
         115                 120                 125

Lys Gln Ile Val Glu Pro Glu Arg Val Ile Thr Phe Arg Val Ser Trp
 130                 135                 140

Leu Asp Asp Ala Gly Asn Leu Gln Val Asn Arg Gly Phe Arg Val Gln
145                 150                 155                 160

Tyr Ser Ser Ala Ile Gly Pro Tyr Lys Gly Gly Leu Arg Phe His Pro
                 165                 170                 175

Ser Val Asn Leu Ser Ile Met Lys Phe Leu Ala Phe Glu Gln Ile Phe
            180                 185                 190

Lys Asn Ser Leu Thr Thr Leu Pro Met Gly Gly Gly Lys Gly Gly Ser
         195                 200                 205

Asp Phe Asp Pro Lys Gly Lys Ser Asp Ala Glu Val Met Arg Phe Cys
         210                 215                 220

Gln Ser Phe Met Thr Glu Leu Gln Arg His Ile Ser Tyr Val Gln Asp
225                 230                 235                 240

Val Pro Ala Gly Asp Ile Gly Val Gly Ala Arg Glu Ile Gly Tyr Leu
                 245                 250                 255

Phe Gly Gln Tyr Lys Arg Ile Thr Lys Asn Tyr Thr Gly Val Leu Thr
            260                 265                 270

Pro Lys Gly Gln Glu Tyr Gly Gly Ser Glu Ile Arg Pro Glu Ala Thr
         275                 280                 285

Gly Tyr Gly Ala Val Leu Phe Val Glu Asn Val Leu Lys Asp Lys Gly
         290                 295                 300

Glu Ser Leu Lys Gly Lys Arg Cys Leu Val Ser Gly Ala Gly Asn Val
305                 310                 315                 320

Ala Gln Tyr Cys Ala Glu Leu Leu Leu Glu Lys Gly Ala Ile Val Leu
                 325                 330                 335

Ser Leu Ser Asp Ser Gln Gly Tyr Val Tyr Glu Pro Asn Gly Phe Thr
            340                 345                 350

Arg Glu Gln Leu Gln Ala Val Gln Asp Met Lys Lys Lys Asn Asn Ser
         355                 360                 365

Ala Arg Ile Ser Glu Tyr Lys Ser Asp Thr Ala Val Tyr Val Gly Asp
 370                 375                 380

Arg Arg Lys Pro Trp Glu Leu Asp Cys Gln Val Asp Ile Ala Phe Pro
385                 390                 395                 400

Cys Ala Thr Gln Asn Glu Ile Asp Glu His Asp Ala Glu Leu Leu Ile
                 405                 410                 415

Lys His Gly Cys Gln Tyr Val Val Glu Gly Ala Asn Met Pro Ser Thr
            420                 425                 430

Asn Glu Ala Ile His Lys Tyr Asn Lys Ala Gly Ile Ile Tyr Cys Pro
         435                 440                 445

Gly Lys Ala Ala Asn Ala Gly Gly Val Ala Val Ser Gly Leu Glu Met
```

-continued

```
                    450                 455                 460
Thr Gln Asn Arg Met Ser Leu Asn Trp Thr Arg Glu Glu Val Arg Asp
465                 470                 475                 480

Lys Leu Glu Arg Ile Met Lys Asp Ile Tyr Asp Ser Ala Met Gly Pro
                485                 490                 495

Ser Arg Arg Tyr Asn Val Asp Leu Ala Ala Gly Ala Asn Ile Ala Gly
            500                 505                 510

Phe Thr Lys Val Ala Asp Ala Val Lys Ala Gln Gly Ala Val
        515                 520                 525

(2) INFORMATION FOR SEQ ID NO: 3:

(i) SEQUENCE CHARACTERISTICS:
        (A) LENGTH: 2099 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 33..1568

(xi) SEQUENCE DESCRIPTION: SEQ ID NO: 3:

CTCCTTTCTG CTCGCCCTCT CTCCGTCCCG CC ATG CAG ACC GCC CTC GTC GCC      53
                                   Met Gln Thr Ala Leu Val Ala
                                    1               5

AAG CCT ATC GTG GCC TGC GCG TGG GTC CGC TCC GCC AAG CGC GAT GTC     101
Lys Pro Ile Val Ala Cys Ala Trp Val Arg Ser Ala Lys Arg Asp Val
         10                  15                  20

CGC GCC AAG GCC GTC TCG CTG GAG GAG CAG ATC TCC GCG ATG GAC GCC     149
Arg Ala Lys Ala Val Ser Leu Glu Glu Gln Ile Ser Ala Met Asp Ala
     25                  30                  35

ACC ACC GGC GAC TTC ACG GCG CTG CAG AAG GCG GTG AAG CAG ATG GCC     197
Thr Thr Gly Asp Phe Thr Ala Leu Gln Lys Ala Val Lys Gln Met Ala
 40                  45                  50                  55

ACC AAG GCG GGC ACT GAG GGC CTG GTG CAC GGC ATC AAG AAC CCC GAC     245
Thr Lys Ala Gly Thr Glu Gly Leu Val His Gly Ile Lys Asn Pro Asp
                 60                  65                  70

GTG CGC CAG CTG CTG ACC GAG ATC TTC ATG AAG GAC CCG GAG CAG CAG     293
Val Arg Gln Leu Leu Thr Glu Ile Phe Met Lys Asp Pro Glu Gln Gln
             75                  80                  85

GAG TTC ATG CAG GCG GTG CGC GAG GTG GCC GTC TCC CTG CAG CCC GTG     341
Glu Phe Met Gln Ala Val Arg Glu Val Ala Val Ser Leu Gln Pro Val
         90                  95                 100

TTC GAG AAG CGC CCC GAG CTG CTG CCC ATC TTC AAG CAG ATC GTT GAG     389
Phe Glu Lys Arg Pro Glu Leu Leu Pro Ile Phe Lys Gln Ile Val Glu
     105                 110                 115

CCT GAG CGC GTG ATC ACC TTC CGC GTG TCC TGG CTG GAC GAC GCC GGC     437
Pro Glu Arg Val Ile Thr Phe Arg Val Ser Trp Leu Asp Asp Ala Gly
120                 125                 130                 135

AAC CTG CAG GTC AAC CGC GGC TTC CGC GTG CAG TAC TCG TCC GCC ATC     485
Asn Leu Gln Val Asn Arg Gly Phe Arg Val Gln Tyr Ser Ser Ala Ile
                 140                 145                 150

GGC CCC TAC AAG GGC GGC CTG CGC TTC CAC CCC TCC GTG AAC CTG TCC     533
Gly Pro Tyr Lys Gly Gly Leu Arg Phe His Pro Ser Val Asn Leu Ser
             155                 160                 165

ATC ATG AAG TTC CTT GCC TTT GAG CAG ATC TTC AAG AAC AGC CTG ACC     581
Ile Met Lys Phe Leu Ala Phe Glu Gln Ile Phe Lys Asn Ser Leu Thr
         170                 175                 180
```

-continued

| | | |
|---|---|---|
| ACC CTG CCC ATG GGC GGC GGC AAG GGC GGC TCC GAC TTC GAC CCC AAG<br>Thr Leu Pro Met Gly Gly Gly Lys Gly Gly Ser Asp Phe Asp Pro Lys<br>185                        190                     195 | 629 |
| GGC AAG AGC GAC GCG GAG GTG ATG CGC TTC TGC CAG TCC TTC ATG ACC<br>Gly Lys Ser Asp Ala Glu Val Met Arg Phe Cys Gln Ser Phe Met Thr<br>200                   205                   210                 215 | 677 |
| GAG CTG CAG CGC CAC ATC AGC TAC GTG CAG GAC GTG CCC GCC GGC GAC<br>Glu Leu Gln Arg His Ile Ser Tyr Val Gln Asp Val Pro Ala Gly Asp<br>                 220                   225                 230 | 725 |
| ATC GGC GTG GGC GCG CGC GAG ATT GGC TAC CTT TTC GGC CAG TAC AAG<br>Ile Gly Val Gly Ala Arg Glu Ile Gly Tyr Leu Phe Gly Gln Tyr Lys<br>              235                   240                   245 | 773 |
| CGC ATC ACC AAG AAC TAC ACC GGC GTG CTG ACC CCG AAG GGC CAG GAG<br>Arg Ile Thr Lys Asn Tyr Thr Gly Val Leu Thr Pro Lys Gly Gln Glu<br>       250                   255                   260 | 821 |
| TAT GGC GGC TCC GAG ATC CGC CCC GAG GCC ACC GGC TAC GGC GCC GTG<br>Tyr Gly Gly Ser Glu Ile Arg Pro Glu Ala Thr Gly Tyr Gly Ala Val<br>265                       270                     275 | 869 |
| CTG TTT GTG GAG AAC GTG CTG AAG GAC AAG GGC GAG AGC CTC AAG GGC<br>Leu Phe Val Glu Asn Val Leu Lys Asp Lys Gly Glu Ser Leu Lys Gly<br>280                      285                 290                 295 | 917 |
| AAG CGC TGC CTG GTG TCT GGC GCG GGC AAC GTG GCC CAG TAC TGC GCG<br>Lys Arg Cys Leu Val Ser Gly Ala Gly Asn Val Ala Gln Tyr Cys Ala<br>                 300                   305                 310 | 965 |
| GAG CTG CTG CTG GAG AAG GGC GCC ATC GTG CTG TCG CTG TCC GAC TCC<br>Glu Leu Leu Leu Glu Lys Gly Ala Ile Val Leu Ser Leu Ser Asp Ser<br>                     315                   320                 325 | 1013 |
| CAG GGC TAC GTG TAC GAG CCC AAC GGC TTC ACG CGC GAG CAG CTG CAG<br>Gln Gly Tyr Val Tyr Glu Pro Asn Gly Phe Thr Arg Glu Gln Leu Gln<br>                 330                   335                 340 | 1061 |
| GCG GTG CAG GAC ATG AAG AAG AAG AAC AAC AGC GCC CGC ATC TCC GAG<br>Ala Val Gln Asp Met Lys Lys Lys Asn Asn Ser Ala Arg Ile Ser Glu<br>345                       350                     355 | 1109 |
| TAC AAG AGC GAC ACC GCC GTG TAT GTG GGC GAC CGC CGC AAG CCT TGG<br>Tyr Lys Ser Asp Thr Ala Val Tyr Val Gly Asp Arg Arg Lys Pro Trp<br>360                       365                   370                 375 | 1157 |
| GAG CTG GAC TGC CAG GTG GAC ATC GCC TTC CCC TGC GCC ACC CAG AAC<br>Glu Leu Asp Cys Gln Val Asp Ile Ala Phe Pro Cys Ala Thr Gln Asn<br>                 380                   385                 390 | 1205 |
| GAG ATC GAT GAG CAC GAC GCC GAG CTG CTG ATC AAG CAC GGC TGC CAG<br>Glu Ile Asp Glu His Asp Ala Glu Leu Leu Ile Lys His Gly Cys Gln<br>               395                   400                 405 | 1253 |
| TAC GTG GTG GAG GGC GCC AAC ATG CCC TCC ACC AAC GAG GCC ATC CAC<br>Tyr Val Val Glu Gly Ala Asn Met Pro Ser Thr Asn Glu Ala Ile His<br>           410                   415                 420 | 1301 |
| AAG TAC AAC AAG GCC GGC ATC ATC TAC TGC CCC GGC AAG GCG GCC AAC<br>Lys Tyr Asn Lys Ala Gly Ile Ile Tyr Cys Pro Gly Lys Ala Ala Asn<br>425                       430                     435 | 1349 |
| GCC GGC GGC GTG GCG GTC AGC GGC CTG GAG ATG ACC CAG AAC CGC ATG<br>Ala Gly Gly Val Ala Val Ser Gly Leu Glu Met Thr Gln Asn Arg Met<br>440                       445                   450                 455 | 1397 |
| AGC CTG AAC TGG ACT CGC GAG GAG GTT CGC GAC AAG CTG GAG CGC ATC<br>Ser Leu Asn Trp Thr Arg Glu Glu Val Arg Asp Lys Leu Glu Arg Ile<br>                 460                   465                 470 | 1445 |
| ATG AAG GAC ATC TAC GAC TCC GCC ATG GGG CCG TCC CGC AGA TAC AAT<br>Met Lys Asp Ile Tyr Asp Ser Ala Met Gly Pro Ser Arg Arg Tyr Asn<br>                     475                   480                 485 | 1493 |
| GTT GAC CTG GCT GCG GGC GCC AAC ATC GCG GGC TTC ACC AAG GTG GCT<br>Val Asp Leu Ala Ala Gly Ala Asn Ile Ala Gly Phe Thr Lys Val Ala<br>           490                   495                 500 | 1541 |

```
GAT GCC GTC AAG GCC CAG GGC GCT GTT TAAGCTGCCC AGGCCCAAGC    1588
Asp Ala Val Lys Ala Gln Gly Ala Val
    505                 510

CACGGCTCAC CGGCAATCCA ACCCAACCAA CTCAACGGCC AGGACCTTTT CGGAAGCG    1648

GCCTTTTTCC CAGCCAGGGC CCTCACCTGC CCTTTCATAA CCCTGCTATT GCCGCCGT    1708

CCCTGCAATT CCACCCCAAG AAGAACTAGC GGCACTTGAC TGCATCAGGA CGGCTATT    1768

TTTCGCGACG CGCGCTCACC CCGAGAGCCT CTCTCCCCCG AGCCCTAAGC GCTGACGT    1828

GCCCGACTTT GCCTCGCACA TCGCTCGGTT TTGACCCCCT CCAGTCTACC CACCCTGT    1888

TGAAGCCTAC CAGCTCAATT GCCTTTTAGT GTATGTGCGC CCCCTCCTGC CCCCGAAT    1948

TCCTGCCATG AGACGTGCGG TTCCTAGCCT GGTGACCCCA AGTAGCAGTT AGTGTGCG    2008

CCTTGCCCTG CGCTGCCCGG GATGCGATAC TGTGACCTGA GAGTGCTTGT GTAAACAC    2068

CGAGTCAAAA AAAAAAAAAA AAAAAAAAA A                                  2099

(2) INFORMATION FOR SEQ ID NO: 4:

(i) SEQUENCE CHARACTERISTICS:
        (A) LENGTH: 512 amino acids
        (B) TYPE: amino acid
        (D) TOPOLOGY: linear (ii) MOLECULE TYPE: protein (xi) SEQUENCE DESCRIPTION: SEQ ID NO: 4:

Met Gln Thr Ala Leu Val Ala Lys Pro Ile Val Ala Cys Ala Trp Val
  1               5                  10                  15

Arg Ser Ala Lys Arg Asp Val Arg Ala Lys Ala Val Ser Leu Glu Glu
             20                  25                  30

Gln Ile Ser Ala Met Asp Ala Thr Thr Gly Asp Phe Thr Ala Leu Gln
         35                  40                  45

Lys Ala Val Lys Gln Met Ala Thr Lys Ala Gly Thr Glu Gly Leu Val
     50                  55                  60

His Gly Ile Lys Asn Pro Asp Val Arg Gln Leu Leu Thr Glu Ile Phe
 65                  70                  75                  80

Met Lys Asp Pro Glu Gln Gln Glu Phe Met Gln Ala Val Arg Glu Val
                 85                  90                  95

Ala Val Ser Leu Gln Pro Val Phe Glu Lys Arg Pro Glu Leu Leu Pro
            100                 105                 110

Ile Phe Lys Gln Ile Val Glu Pro Glu Arg Val Ile Thr Phe Arg Val
        115                 120                 125

Ser Trp Leu Asp Asp Ala Gly Asn Leu Gln Val Asn Arg Gly Phe Arg
    130                 135                 140

Val Gln Tyr Ser Ser Ala Ile Gly Pro Tyr Lys Gly Gly Leu Arg Phe
145                 150                 155                 160

His Pro Ser Val Asn Leu Ser Ile Met Lys Phe Leu Ala Phe Glu Gln
                165                 170                 175

Ile Phe Lys Asn Ser Leu Thr Thr Leu Pro Met Gly Gly Gly Lys Gly
            180                 185                 190

Gly Ser Asp Phe Asp Pro Lys Gly Lys Ser Asp Ala Glu Val Met Arg
        195                 200                 205

Phe Cys Gln Ser Phe Met Thr Glu Leu Gln Arg His Ile Ser Tyr Val
    210                 215                 220

Gln Asp Val Pro Ala Gly Asp Ile Gly Val Gly Ala Arg Glu Ile Gly
225                 230                 235                 240
```

```
Tyr Leu Phe Gly Gln Tyr Lys Arg Ile Thr Lys Asn Tyr Thr Gly Val
                245                 250                 255

Leu Thr Pro Lys Gly Gln Glu Tyr Gly Gly Ser Glu Ile Arg Pro Glu
                260                 265                 270

Ala Thr Gly Tyr Gly Ala Val Leu Phe Val Glu Asn Val Leu Lys Asp
                275                 280                 285

Lys Gly Glu Ser Leu Lys Gly Lys Arg Cys Leu Val Ser Gly Ala Gly
                290                 295                 300

Asn Val Ala Gln Tyr Cys Ala Glu Leu Leu Leu Glu Lys Gly Ala Ile
305                 310                 315                 320

Val Leu Ser Leu Ser Asp Ser Gln Gly Tyr Val Tyr Glu Pro Asn Gly
                325                 330                 335

Phe Thr Arg Glu Gln Leu Gln Ala Val Gln Asp Met Lys Lys Lys Asn
                340                 345                 350

Asn Ser Ala Arg Ile Ser Glu Tyr Lys Ser Asp Thr Ala Val Tyr Val
                355                 360                 365

Gly Asp Arg Arg Lys Pro Trp Glu Leu Asp Cys Gln Val Asp Ile Ala
370                 375                 380

Phe Pro Cys Ala Thr Gln Asn Glu Ile Asp Glu His Asp Ala Glu Leu
385                 390                 395                 400

Leu Ile Lys His Gly Cys Gln Tyr Val Val Glu Gly Ala Asn Met Pro
                405                 410                 415

Ser Thr Asn Glu Ala Ile His Lys Tyr Asn Lys Ala Gly Ile Ile Tyr
                420                 425                 430

Cys Pro Gly Lys Ala Ala Asn Ala Gly Gly Val Ala Val Ser Gly Leu
                435                 440                 445

Glu Met Thr Gln Asn Arg Met Ser Leu Asn Trp Thr Arg Glu Glu Val
                450                 455                 460

Arg Asp Lys Leu Glu Arg Ile Met Lys Asp Ile Tyr Asp Ser Ala Met
465                 470                 475                 480

Gly Pro Ser Arg Arg Tyr Asn Val Asp Leu Ala Ala Gly Ala Asn Ile
                485                 490                 495

Ala Gly Phe Thr Lys Val Ala Asp Ala Val Lys Ala Gln Gly Ala Val
                500                 505                 510

(2) INFORMATION FOR SEQ ID NO: 5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Ala Val Ser Leu Glu Glu Gln Ile Ser Ala Met Asp Ala Thr Thr Gl
1               5                   10                  15

Asp Phe Thr Ala
            20

(2) INFORMATION FOR SEQ ID NO: 6:

(i) SEQUENCE CHARACTERISTICS:
        (A) LENGTH: 10 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO: 6:

```
Asp Ala Thr Thr Gly Asp Phe Thr Ala Leu
1               5                   10
```

(2) INFORMATION FOR SEQ ID NO: 7:

(i) SEQUENCE CHARACTERISTICS:
        (A) LENGTH: 1969 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 7:

```
CAGATCTCCG CGATGGACGC CACCACCGGC GACTTCACGG CGCTGCAGAA GGCGGTGAAG      60
CAGATGGCCA CCAAGGCGGG CACTGAGGGC CTGGTGCACG GCATCAAGAA CCCCGACGT      120
CGCCAGCTGC TGACCGAGAT CTTCATGAAG GACCCGGAGC AGCAGGAGTT CATGCAGGC      180
GTGCGCGAGG TGGCCGTCTC CCTGCAGCCC GTGTTCGAGA AGCGCCCCGA GCTGCTGCC      240
ATCTTCAAGC AGATCGTTGA GCCTGAGCGC GTGATCACCT TCCGCGTGTC CTGGCTGGA      300
GACGCCGGCA ACCTGCAGGT CAACCGCGGC TTCCGCGTGC AGTACTCGTC CGCCATCGG      360
CCCTACAAGG GCGGCCTGCG CTTCCACCCC TCCGTGAACC TGTCCATCAT GAAGTTCCT      420
GCCTTTGAGC AGATCTTCAA GAACAGCCTG ACCACCCTGC CCATGGGCGG CGGCAAGGG      480
GGCTCCGACT TCGACCCCAA GGGCAAGAGC GACGCGGAGG TGATGCGCTT CTGCCAGTC      540
TTCATGACCG AGCTGCAGCG CCACATCAGC TACGTGCAGG ACGTGCCCGC CGGCGACAT      600
GGCGTGGGCG CGCGCGAGAT TGGCTACCTT TTCGGCCAGT ACAAGCGCAT CACCAAGAA      660
TACACCGGCG TGCTGACCCC GAAGGGCCAG GAGTATGGCG GCTCCGAGAT CCGCCCCGA      720
GCCACCGGCT ACGGCGCCGT GCTGTTTGTG GAGAACGTGC TGAAGGACAA GGGCGAGAG      780
CTCAAGGGCA AGCGCTGCCT GGTGTCTGGC GCGGGCAACG TGGCCCAGTA CTGCGCGGA      840
CTGCTGCTGG AGAAGGGCGC CATCGTGCTG TCGCTGTCCG ACTCCCAGGG CTACGTGTA      900
GAGCCCAACG GCTTCACGCG CGAGCAGCTG CAGGCGGTGC AGGACATGAA GAAGAAGAA      960
AACAGCGCCC GCATCTCCGA GTACAAGAGC GACACCGCCG TGTATGTGGG CGACCGCC      1020
AAGCCTTGGG AGCTGGACTG CCAGGTGGAC ATCGCCTTCC CCTGCGCCAC CCAGAACG      1080
ATCGATGAGC ACGACGCCGA GCTGCTGATC AAGCACGGCT GCCAGTACGT GGTGGAGG      1140
GCCAACATGC CCTCCACCAA CGAGGCCATC ACAAGTACA CAAGGCCGG CATCATCT       1200
TGCCCCGGCA AGGCGGCCAA CGCCGGCGGC GTGGCGGTCA GCGGCCTGGA GATGACCC      1260
AACCGCATGA GCCTGAACTG GACTCGCGAG GAGGTTCGCG ACAAGCTGGA GCGCATCA      1320
AAGGACATCT ACGACTCCGC CATGGGCCGG TCCCGCAGAT ACAATGTTGA CCTGGCTG      1380
GGCGCCAACA TCGCGGGCTT CACCAAGGTG GCTGATGCCG TCAAGGCCCA GGGCGCTG      1440
TAAGCTGCCC AGGCCCAAGC CACGGCTCAC CGGCAATCCA ACCCAACCAA CTCAACGG      1500
AGGACCTTTT CGGAAGCGGC GCCTTTTTCC CAGCCAGGGC CCTCACCTGC CCTTTCAT      1560
CCCTGCTATT GCCGCCGTGC CCCTGCAATT CCACCCCAAG AAGAACTAGC GGCACTTG      1620
TGCATCAGGA CGGCTATTTT TTTCGCGACG CGCGCTCACC CCGAGAGCCT CTCTCCCC      1680
AGCCCTAAGC GCTGACGTCC GCCCGACTTT GCCTCGCACA TCGCTCGGTT TTGACCCC      1740
```

```
CCAGTCTACC CACCCTGTTG TGAAGCCTAC CAGCTCAATT GCCTTTTAGT GTATGTGC         1800

CCCCTCCTGC CCCCGAATTT TCCTGCCATG AGACGTGCGG TTCCTAGCCT GGTGACCC         1860

AGTAGCAGTT AGTGTGCGTG CCTTGCCCTG CGCTGCCCGG GATGCGATAC TGTGACCT         1920

GAGTGCTTGT GTAAACACGA CGAGTCAAAA AAAAAAAAA AAAAAAAA                     1969
```

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 8:

```
CTCAAAGGCA AGGAACTTCA TG                                                22
```

(2) INFORMATION FOR SEQ ID NO: 9:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

```
GGGTCGACAT TCTAGACAGA ATTCGTGGAT CCTTTTTTTT TTTTTTTTT                   50
```

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 10:

```
GGACGAGTAC TGCACGC                                                      17
```

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 11:

```
GATCTCGGTC AGCAGCTG                                                     18
```

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 12:

GGGTCGACAT TCTAGACAGA A                                              21

(2) INFORMATION FOR SEQ ID NO: 13:

(i) SEQUENCE CHARACTERISTICS:
        (A) LENGTH: 367 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 13:

GGGTCGACAT TCTAGACAGA ATTCGTGGAT CCTTTTTTTT TTTTTTTTTT TTTTTTCTCC    60
TTTCTGCTCG CCCTCTCTCC GTCCCGCCAT GCAGACCGCC CTCGTCGCCA AGCCTATCG    120
GGCCGCCCCG CTGGCGGCAC GCCCGCGCTG CCTCGCGCCG TGGCCGTGCG CGTGGGTCC    180
CTCCGCCAAG CGCGATGTCC GCGCCAAGGC CGTCTCGCTG GAGGAGCAGA TCTCCGCGA    240
GGACGCCACC ACCGGCGACT TCACGGCGCT GCAGAAGGCG GTGAAGCAGA TGGCCACCA    300
GGCGGGCACT GAGGGCCTGG TGCACGGCAT CAAGAACCCC GACGTGCGCC AGCTGCTGA    360
CGAGATC                                                              367

(2) INFORMATION FOR SEQ ID NO: 14:

(i) SEQUENCE CHARACTERISTICS:
        (A) LENGTH: 325 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 14:

GGGTCGACAT TCTAGACAGA ATTCGTGGAT CCTTTTTTTT TTTTTTTTTT TTTTTTCTCC    60
TTTCTGCTCG CCCTCTCTCC GTCCCGCCAT GCAGACCGCC CTCGTCGCCA AGCCTATCG    120
GGCCTGCGCG TGGGTCCGCT CCGCCAAGCG CGATGTCCGC GCCAAGGCCG TCTCGCTGG    180
GGAGCAGATC TCCGCGATGG ACGCCACCAC CGGCGACTTC ACGGCGCTGC AGAAGGCGG    240
GAAGCAGATG GCCACCAAGG CGGGCACTGA GGGCCTGGTG CACGGCATCA AGAACCCCG    300
CGTGCGCCAG CTGCTGACCG AGATC                                         325

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 15:

CTTTCTGCTC GCCCTCTC                                                  18

(2) INFORMATION FOR SEQ ID NO: 16:

(i) SEQUENCE CHARACTERISTICS:
        (A) LENGTH: 308 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 16:

```
CTTTCTGCTC GCCCTCTCTC CGTCCCGCCA TGCAGACCGC CCTCGTCGCC AAGCCTATCG      60
TGGCCGCCCC GCTGGCGGCA CGCCCGCGCT GCCTCGCGCC GTGGCCGTGC GCGTGGGTC      120
GCTCCGCCAA GCGCGATGTC CGCGCCAAGG CCGTCTCGCT GGAGGAGCAG ATCTCCGCG      180
TGGACGCCAC CACCGGCGAC TTCACGGCGC TGCAGAAGGC GGTGAAGCAG ATGGCCACC      240
AGGCGGGCAC TGAGGGCCTG GTGCACGGCA TCAAGAACCC CGACGTGCGC CAGCTGCTG      300
CCGAGATC                                                              308
```

(2) INFORMATION FOR SEQ ID NO: 17:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 17:

```
CTTTCTGCTC GCCCTCTCTC CGTCCCGCCA TGCAGACCGC CCTCGTCGCC AAGCCTATCG      60
TGGCCTGCGC GTGGGTCCGC TCCGCCAAGC GCGATGTCCG CGCCAAGGCC GTCTCGCTG      120
AGGAGCAGAT CTCCGCGATG GACGCCACCA CCGGCGACTT CACGGCGCTG CAGAAGGCG      180
TGAAGCAGAT GGCCACCAAG GCGGGCACTG AGGGCCTGGT GCACGGCATC AAGAACCCC      240
ACGTGCGCCA GCTGCTGACC GAGATC                                          266
```

(2) INFORMATION FOR SEQ ID NO: 18:

(i) SEQUENCE CHARACTERISTICS:
        (A) LENGTH: 2137 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 18:

```
CTTTCTGCTC GCCCTCTCTC CGTCCCGCCA TGCAGACCGC CCTCGTCGCC AAGCCTATCG      60
TGGCCGCCCC GCTGGCGGCA CGCCCGCGCT GCCTCGCGCC GTGGCCGTGC GCGTGGGTC      120
GCTCCGCCAA GCGCGATGTC CGCGCCAAGG CCGTCTCGCT GGAGGAGCAG ATCTCCGCG      180
TGGACGCCAC CACCGGCGAC TTCACGGCGC TGCAGAAGGC GGTGAAGCAG ATGGCCACC      240
AGGCGGGCAC TGAGGGCCTG GTGCACGGCA TCAAGAACCC CGACGTGCGC CAGCTGCTG      300
CCGAGATCTT CATGAAGGAC CCGGAGCAGC AGGAGTTCAT GCAGGCGGTG CGCGAGGTG      360
CCGTCTCCCT GCAGCCCGTG TTCGAGAAGC GCCCCGAGCT GCTGCCCATC TTCAAGCAG      420
TCGTTGAGCC TGAGCGCGTG ATCACCTTCC GCGTGTCCTG GCTGGACGAC GCCGGCAAC      480
TGCAGGTCAA CCGCGGCTTC CGCGTGCAGT ACTCGTCCGC CATCGGCCCC TACAAGGGC      540
GCCTGCGCTT CCACCCCTCC GTGAACCTGT CCATCATGAA GTTCCTTGCC TTTGAGCAG      600
TCTTCAAGAA CAGCCTGACC ACCCTGCCCA TGGGCGGCGG CAAGGGCGGC TCCGACTTC      660
ACCCCAAGGG CAAGAGCGAC GCGGAGGTGA TGCGCTTCTG CCAGTCCTTC ATGACCGAG      720
TGCAGCGCCA CATCAGCTAC GTGCAGGACG TGCCCGCCGG CGACATCGGC GTGGGCGCG      780
```

```
GCGAGATTGG CTACCTTTTC GGCCAGTACA AGCGCATCAC CAAGAACTAC ACCGGCGTG   840

TGACCCCGAA GGGCCAGGAG TATGGCGGCT CCGAGATCCG CCCCGAGGCC ACCGGCTAC   900

GCGCCGTGCT GTTTGTGGAG AACGTGCTGA AGGACAAGGG CGAGAGCCTC AAGGGCAAG   960

GCTGCCTGGT GTCTGGCGCG GGCAACGTGG CCCAGTACTG CGCGGAGCTG CTGCTGGA   1020

AGGGCGCCAT CGTGCTGTCG CTGTCCGACT CCCAGGGCTA CGTGTACGAG CCCAACGG   1080

TCACGCGCGA GCAGCTGCAG GCGGTGCAGG ACATGAAGAA GAAGAACAAC AGCGCCCG   1140

TCTCCGAGTA CAAGAGCGAC ACCGCCGTGT ATGTGGGCGA CCGCCGCAAG CCTTGGGA   1200

TGGACTGCCA GGTGGACATC GCCTTCCCCT GCGCCACCCA GAACGAGATC GATGAGCA   1260

ACGCCGAGCT GCTGATCAAG CACGGCTGCC AGTACGTGGT GGAGGGCGCC AACATGCC   1320

CCACCAACGA GGCCATCCAC AAGTACAACA AGGCCGGCAT CATCTACTGC CCCGGCAA   1380

CGGCCAACGC CGGCGGCGTG GCGGTCAGCG GCCTGGAGAT GACCCAGAAC CGCATGAG   1440

TGAACTGGAC TCGCGAGGAG GTTCGCGACA GCTGGAGCG CATCATGAAG GACATCTA   1500

ACTCCGCCAT GGGGCCGTCC CGCAGATACA ATGTTGACCT GGCTGCGGGC GCCAACAT   1560

CGGGCTTCAC CAAGGTGGCT GATGCCGTCA AGGCCCAGGG CGCTGTTTAA GCTGCCCA   1620

CCCAAGCCAC GGCTCACCGG CAATCCAACC CAACCAACTC AACGGCCAGG ACCTTTTC   1680

AAGCGGCGCC TTTTTCCCAG CCAGGGCCCT CACCTGCCCT TTCATAACCC TGCTATTG   1740

GCCGTGCCCC TGCAATTCCA CCCCAAGAAG AACTAGCGGC ACTTGACTGC ATCAGGAC   1800

CTATTTTTTT CGCGACGCGC GCTCACCCCG AGAGCCTCTC TCCCCCGAGC CCTAAGCG   1860

GACGTCCGCC CGACTTTGCC TCGCACATCG CTCGGTTTTG ACCCCTCCA GTCTACCC   1920

CCTGTTGTGA AGCCTACCAG CTCAATTGCC TTTTAGTGTA TGTGCGCCCC CTCCTGCC   1980

CGAATTTTCC TGCCATGAGA CGTGCGGTTC CTAGCCTGGT GACCCCAAGT AGCAGTTA   2040

GTGCGTGCCT TGCCCTGCGC TGCCCGGGAT GCGATACTGT GACCTGAGAG TGCTTGTG   2100

AACACGACGA GTCAAAAAAA AAAAAAAAAA AAAAAA                          2137
```

(2) INFORMATION FOR SEQ ID NO: 19:

(i) SEQUENCE CHARACTERISTICS:
        (A) LENGTH: 2096 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 19:

```
CTTTCTGCTC GCCCTCTCTC CGTCCCGCCA TGCAGACCGC CCTCGTCGCC AAGCCTATCG    60

TGGCCTGCGC GTGGGTCCGC TCCGCCAAGC GCGATGTCCG CGCCAAGGCC GTCTCGCTG    120

AGGAGCAGAT CTCCGCGATG GACGCCACCA CCGGCGACTT CACGGCGCTG CAGAAGGCG    180

TGAAGCAGAT GGCCACCAAG GCGGGCACTG AGGGCCTGGT GCACGGCATC AAGAACCCC    240

ACGTGCGCCA GCTGCTGACC GAGATCTTCA TGAAGGACCC GGAGCAGCAG GAGTTCATG    300

AGGCGGTGCG CGAGGTGGCC GTCTCCCTGC AGCCCGTGTT CGAGAAGCGC CCCGAGCTG    360

TGCCCATCTT CAAGCAGATC GTTGAGCCTG AGCGCGTGAT CACCTTCCGC GTGTCCTGG    420

TGGACGACGC CGGCAACCTG CAGGTCAACC GCGGCTTCCG CGTGCAGTAC TCGTCCGCC    480

TCGGCCCCTA CAAGGGCGGC CTGCGCTTCC ACCCCTCCGT GAACCTGTCC ATCATGAAG    540

TCCTTGCCTT TGAGCAGATC TTCAAGAACA GCCTGACCAC CCTGCCCATG GGCGGCGGC    600
```

```
AGGGCGGCTC CGACTTCGAC CCCAAGGGCA AGAGCGACGC GGAGGTGATG CGCTTCTGC      660

AGTCCTTCAT GACCGAGCTG CAGCGCCACA TCAGCTACGT GCAGGACGTG CCCGCCGGC      720

ACATCGGCGT GGGCGCGCGC GAGATTGGCT ACCTTTTCGG CCAGTACAAG CGCATCACC      780

AGAACTACAC CGGCGTGCTG ACCCCGAAGG GCCAGGAGTA TGGCGGCTCC GAGATCCGC      840

CCGAGGCCAC CGGCTACGGC GCCGTGCTGT TTGTGGAGAA CGTGCTGAAG GACAAGGGC      900

AGAGCCTCAA GGGCAAGCGC TGCCTGGTGT CTGGCGCGGG CAACGTGGCC CAGTACTGC      960

CGGAGCTGCT GCTGGAGAAG GGCGCCATCG TGCTGTCGCT GTCCGACTCC CAGGGCTA     1020

TGTACGAGCC CAACGGCTTC ACGCGCGAGC AGCTGCAGGC GGTGCAGGAC ATGAAGAA     1080

AGAACAACAG CGCCCGCATC TCCGAGTACA AGAGCGACAC CGCCGTGTAT GTGGGCGA     1140

GCCGCAAGCC TTGGGAGCTG GACTGCCAGG TGGACATCGC CTTCCCCTGC GCCACCCA     1200

ACGAGATCGA TGAGCACGAC GCCGAGCTGC TGATCAAGCA CGGCTGCCAG TACGTGGT     1260

AGGGCGCCAA CATGCCCTCC ACCAACGAGG CCATCCACAA GTACAACAAG GCCGGCAT     1320

TCTACTGCCC CGGCAAGGCG GCCAACGCCG GCGGCGTGGC GGTCAGCGGC CTGGAGAT     1380

CCCAGAACCG CATGAGCCTG AACTGGACTC GCGAGGAGGT TCGCGACAAG CTGGAGCG     1440

TCATGAAGGA CATCTACGAC TCCGCCATGG GGCCGTCCCG CAGATACAAT GTTGACCT     1500

CTGCGGGCGC CAACATCGCG GGCTTCACCA AGGTGGCTGA TGCCGTCAAG GCCCAGGG     1560

CTGTTTAAGC TGCCCAGGCC CAAGCCACGG CTCACCGGCA ATCCAACCCA ACCAACTC     1620

CGGCCAGGAC CTTTTCGGAA GCGGCGCCTT TTTCCCAGCC AGGGCCCTCA CCTGCCCT     1680

CATAACCCTG CTATTGCCGC CGTGCCCCTG CAATTCCACC CCAAGAAGAA CTAGCGGC     1740

TTGACTGCAT CAGGACGGCT ATTTTTTTCG CGACGCGCGC TCACCCCGAG AGCCTCTC     1800

CCCCGAGCCC TAAGCGCTGA CGTCCGCCCG ACTTTGCCTC GCACATCGCT CGGTTTTG     1860

CCCCTCCAGT CTACCCACCC TGTTGTGAAG CCTACCAGCT CAATTGCCTT TTAGTGTA     1920

TGCGCCCCCT CCTGCCCCCG AATTTTCCTG CCATGAGACG TGCGGTTCCT AGCCTGGT     1980

CCCCAAGTAG CAGTTAGTGT GCGTGCCTTG CCCTGCGCTG CCCGGGATGC GATACTGT     2040

CCTGAGAGTG CTTGTGTAAA CACGACGAGT CAAAAAAAAA AAAAAAAAAA AAAAAA      2096

(2) INFORMATION FOR SEQ ID NO: 20:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 20:

CATATGGCCG TCTCGCTGGG AGGAG                                            25

(2) INFORMATION FOR SEQ ID NO: 21:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 21:

GTTGGATTGC CGGTGAGCC                                                   19
```

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: CDNA (xi) SEQUENCE DESCRIPTION: SEQ ID NO: 22:

```
CATATGGACG CCACCACCGG C                                             21
```

(2) INFORMATION FOR SEQ ID NO: 23:

(i) SEQUENCE CHARACTERISTICS:
        (A) LENGTH: 1506 base pairs
        (B) TYPE: nucleic acid
        (C) STRANDEDNESS: double
        (D) TOPOLOGY: linear (ii) MOLECULE TYPE: CDNA (ix) FEATURE:
        (A) NAME/KEY: CDS
        (B) LOCATION: 4..1464

(xi) SEQUENCE DESCRIPTION: SEQ ID NO: 23:

```
CAT ATG GCC GTC TCG CTG GAG GAG CAG ATC TCC GCG ATG GAC GCC ACC       48
    Met Ala Val Ser Leu Glu Glu Gln Ile Ser Ala Met Asp Ala Thr
            515                 520                 525

ACC GGC GAC TTC ACG GCG CTG CAG AAG GCG GTG AAG CAG ATG GCC ACC       96
Thr Gly Asp Phe Thr Ala Leu Gln Lys Ala Val Lys Gln Met Ala Thr
            530                 535                 540

AAG GCG GGC ACT GAG GGC CTG GTG CAC GGC ATC AAG AAC CCC GAC GTG      144
Lys Ala Gly Thr Glu Gly Leu Val His Gly Ile Lys Asn Pro Asp Val
545                 550                 555

CGC CAG CTG CTG ACC GAG ATC TTC ATG AAG GAC CCG GAG CAG CAG GAG      192
Arg Gln Leu Leu Thr Glu Ile Phe Met Lys Asp Pro Glu Gln Gln Glu
560                 565                 570                 575

TTC ATG CAG GCG GTG CGC GAG GTG GCC GTC TCC CTG CAG CCC GTG TTC      240
Phe Met Gln Ala Val Arg Glu Val Ala Val Ser Leu Gln Pro Val Phe
            580                 585                 590

GAG AAG CGC CCC GAG CTG CTG CCC ATC TTC AAG CAG ATC GTT GAG CCT      288
Glu Lys Arg Pro Glu Leu Leu Pro Ile Phe Lys Gln Ile Val Glu Pro
            595                 600                 605

GAG CGC GTG ATC ACC TTC CGC GTG TCC TGG CTG GAC GAC GCC GGC AAC      336
Glu Arg Val Ile Thr Phe Arg Val Ser Trp Leu Asp Asp Ala Gly Asn
            610                 615                 620

CTG CAG GTC AAC CGC GGC TTC CGC GTG CAG TAC TCG TCC GCC ATC GGC      384
Leu Gln Val Asn Arg Gly Phe Arg Val Gln Tyr Ser Ser Ala Ile Gly
625                 630                 635

CCC TAC AAG GGC GGC CTG CGC TTC CAC CCC TCC GTG AAC CTG TCC ATC      432
Pro Tyr Lys Gly Gly Leu Arg Phe His Pro Ser Val Asn Leu Ser Ile
640                 645                 650                 655

ATG AAG TTC CTT GCC TTT GAG CAG ATC TTC AAG AAC AGC CTG ACC ACC      480
Met Lys Phe Leu Ala Phe Glu Gln Ile Phe Lys Asn Ser Leu Thr Thr
            660                 665                 670

CTG CCC ATG GGC GGC GGC AAG GGC GGC TCC GAC TTC GAC CCC AAG GGC      528
Leu Pro Met Gly Gly Gly Lys Gly Gly Ser Asp Phe Asp Pro Lys Gly
            675                 680                 685

AAG AGC GAC GCG GAG GTG ATG CGC TTC TGC CAG TCC TTC ATG ACC GAG      576
Lys Ser Asp Ala Glu Val Met Arg Phe Cys Gln Ser Phe Met Thr Glu
```

-continued

```
                690             695              700
CTG CAG CGC CAC ATC AGC TAC GTG CAG GAC GTG CCC GCC GGC GAC ATC        624
Leu Gln Arg His Ile Ser Tyr Val Gln Asp Val Pro Ala Gly Asp Ile
        705                 710                 715

GGC GTG GGC GCG CGC GAG ATT GGC TAC CTT TTC GGC CAG TAC AAG CGC        672
Gly Val Gly Ala Arg Glu Ile Gly Tyr Leu Phe Gly Gln Tyr Lys Arg
720                 725                 730                 735

ATC ACC AAG AAC TAC ACC GGC GTG CTG ACC CCG AAG GGC CAG GAG TAT        720
Ile Thr Lys Asn Tyr Thr Gly Val Leu Thr Pro Lys Gly Gln Glu Tyr
                740                 745                 750

GGC GGC TCC GAG ATC CGC CCC GAG GCC ACC GGC TAC GGC GCC GTG CTG        768
Gly Gly Ser Glu Ile Arg Pro Glu Ala Thr Gly Tyr Gly Ala Val Leu
        755                 760                 765

TTT GTG GAG AAC GTG CTG AAG GAC AAG GGC GAG AGC CTC AAG GGC AAG        816
Phe Val Glu Asn Val Leu Lys Asp Lys Gly Glu Ser Leu Lys Gly Lys
                770                 775                 780

CGC TGC CTG GTG TCT GGC GCG GGC AAC GTG GCC CAG TAC TGC GCG GAG        864
Arg Cys Leu Val Ser Gly Ala Gly Asn Val Ala Gln Tyr Cys Ala Glu
        785                 790                 795

CTG CTG CTG GAG AAG GGC GCC ATC GTG CTG TCG CTG TCC GAC TCC CAG        912
Leu Leu Leu Glu Lys Gly Ala Ile Val Leu Ser Leu Ser Asp Ser Gln
800                 805                 810                 815

GGC TAC GTG TAC GAG CCC AAC GGC TTC ACG CGC GAG CAG CTG CAG GCG        960
Gly Tyr Val Tyr Glu Pro Asn Gly Phe Thr Arg Glu Gln Leu Gln Ala
                820                 825                 830

GTG CAG GAC ATG AAG AAG AAG AAC AAC AGC GCC CGC ATC TCC GAG TAC       1008
Val Gln Asp Met Lys Lys Lys Asn Asn Ser Ala Arg Ile Ser Glu Tyr
        835                 840                 845

AAG AGC GAC ACC GCC GTG TAT GTG GGC GAC CGC CGC AAG CCT TGG GAG       1056
Lys Ser Asp Thr Ala Val Tyr Val Gly Asp Arg Arg Lys Pro Trp Glu
                850                 855                 860

CTG GAC TGC CAG GTG GAC ATC GCC TTC CCC TGC GCC ACC CAG AAC GAG       1104
Leu Asp Cys Gln Val Asp Ile Ala Phe Pro Cys Ala Thr Gln Asn Glu
        865                 870                 875

ATC GAT GAG CAC GAC GCC GAG CTG CTG ATC AAG CAC GGC TGC CAG TAC       1152
Ile Asp Glu His Asp Ala Glu Leu Leu Ile Lys His Gly Cys Gln Tyr
880                 885                 890                 895

GTG GTG GAG GGC GCC AAC ATG CCC TCC ACC AAC GAG GCC ATC CAC AAG       1200
Val Val Glu Gly Ala Asn Met Pro Ser Thr Asn Glu Ala Ile His Lys
                900                 905                 910

TAC AAC AAG GCC GGC ATC ATC TAC TGC CCC GGC AAG GCG GCC AAC GCC       1248
Tyr Asn Lys Ala Gly Ile Ile Tyr Cys Pro Gly Lys Ala Ala Asn Ala
        915                 920                 925

GGC GGC GTG GCG GTC AGC GGC CTG GAG ATG ACC CAG AAC CGC ATG AGC       1296
Gly Gly Val Ala Val Ser Gly Leu Glu Met Thr Gln Asn Arg Met Ser
930                 935                 940

CTG AAC TGG ACT CGC GAG GAG GTT CGC GAC AAG CTG GAG CGC ATC ATG       1344
Leu Asn Trp Thr Arg Glu Glu Val Arg Asp Lys Leu Glu Arg Ile Met
        945                 950                 955

AAG GAC ATC TAC GAC TCC GCC ATG GGG CCG TCC CGC AGA TAC AAT GTT       1392
Lys Asp Ile Tyr Asp Ser Ala Met Gly Pro Ser Arg Arg Tyr Asn Val
960                 965                 970                 975

GAC CTG GCT GCG GGC GCC AAC ATC GCG GGC TTC ACC AAG GTG GCT GAT       1440
Asp Leu Ala Ala Gly Ala Asn Ile Ala Gly Phe Thr Lys Val Ala Asp
                980                 985                 990

GCC GTC AAG GCC CAG GGC GCT GTT TAAGCTGCCC AGGCCCAAGC CACGGCTCA       1494
Ala Val Lys Ala Gln Gly Ala Val
        995

CGGCAATCCA AC                                                        1506
```

(2) INFORMATION FOR SEQ ID NO: 24:

(i) SEQUENCE CHARACTERISTICS:
        (A) LENGTH: 487 amino acids
        (B) TYPE: amino acid
        (D) TOPOLOGY: linear (ii) MOLECULE TYPE: protein (xi) SEQUENCE DESCRIPTION: SEQ ID NO: 24:

```
Met Ala Val Ser Leu Glu Glu Gln Ile Ser Ala Met Asp Ala Thr Thr
 1               5                  10                  15

Gly Asp Phe Thr Ala Leu Gln Lys Ala Val Lys Gln Met Ala Thr Lys
             20                  25                  30

Ala Gly Thr Glu Gly Leu Val His Gly Ile Lys Asn Pro Asp Val Arg
         35                  40                  45

Gln Leu Leu Thr Glu Ile Phe Met Lys Asp Pro Glu Gln Gln Glu Phe
     50                  55                  60

Met Gln Ala Val Arg Glu Val Ala Val Ser Leu Gln Pro Val Phe Glu
 65                  70                  75                  80

Lys Arg Pro Glu Leu Leu Pro Ile Phe Lys Gln Ile Val Glu Pro Glu
                 85                  90                  95

Arg Val Ile Thr Phe Arg Val Ser Trp Leu Asp Asp Ala Gly Asn Leu
            100                 105                 110

Gln Val Asn Arg Gly Phe Arg Val Gln Tyr Ser Ser Ala Ile Gly Pro
        115                 120                 125

Tyr Lys Gly Gly Leu Arg Phe His Pro Ser Val Asn Leu Ser Ile Met
    130                 135                 140

Lys Phe Leu Ala Phe Glu Gln Ile Phe Lys Asn Ser Leu Thr Thr Leu
145                 150                 155                 160

Pro Met Gly Gly Gly Lys Gly Gly Ser Asp Phe Asp Pro Lys Gly Lys
                165                 170                 175

Ser Asp Ala Glu Val Met Arg Phe Cys Gln Ser Phe Met Thr Glu Leu
            180                 185                 190

Gln Arg His Ile Ser Tyr Val Gln Asp Val Pro Ala Gly Asp Ile Gly
        195                 200                 205

Val Gly Ala Arg Glu Ile Gly Tyr Leu Phe Gly Gln Tyr Lys Arg Ile
    210                 215                 220

Thr Lys Asn Tyr Thr Gly Val Leu Thr Pro Lys Gly Gln Glu Tyr Gly
225                 230                 235                 240

Gly Ser Glu Ile Arg Pro Glu Ala Thr Gly Tyr Gly Ala Val Leu Phe
                245                 250                 255

Val Glu Asn Val Leu Lys Asp Lys Gly Glu Ser Leu Lys Gly Lys Arg
            260                 265                 270

Cys Leu Val Ser Gly Ala Gly Asn Val Ala Gln Tyr Cys Ala Glu Leu
        275                 280                 285

Leu Leu Glu Lys Gly Ala Ile Val Leu Ser Leu Ser Asp Ser Gln Gly
    290                 295                 300

Tyr Val Tyr Glu Pro Asn Gly Phe Thr Arg Glu Gln Leu Gln Ala Val
305                 310                 315                 320

Gln Asp Met Lys Lys Lys Asn Asn Ser Ala Arg Ile Ser Glu Tyr Lys
                325                 330                 335

Ser Asp Thr Ala Val Tyr Val Gly Asp Arg Arg Lys Pro Trp Glu Leu
            340                 345                 350
```

```
Asp Cys Gln Val Asp Ile Ala Phe Pro Cys Ala Thr Gln Asn Glu Ile
        355                 360                 365

Asp Glu His Asp Ala Glu Leu Leu Ile Lys His Gly Cys Gln Tyr Val
370                 375                 380

Val Glu Gly Ala Asn Met Pro Ser Thr Asn Glu Ala Ile His Lys Tyr
385                 390                 395                 400

Asn Lys Ala Gly Ile Ile Tyr Cys Pro Gly Lys Ala Ala Asn Ala Gly
                405                 410                 415

Gly Val Ala Val Ser Gly Leu Glu Met Thr Gln Asn Arg Met Ser Leu
                420                 425                 430

Asn Trp Thr Arg Glu Glu Val Arg Asp Lys Leu Glu Arg Ile Met Lys
        435                 440                 445

Asp Ile Tyr Asp Ser Ala Met Gly Pro Ser Arg Arg Tyr Asn Val Asp
450                 455                 460

Leu Ala Ala Gly Ala Asn Ile Ala Gly Phe Thr Lys Val Ala Asp Ala
465                 470                 475                 480

Val Lys Ala Gln Gly Ala Val
                485

(2) INFORMATION FOR SEQ ID NO: 25:

(i) SEQUENCE CHARACTERISTICS:
        (A) LENGTH: 1473 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 4..1431

(xi) SEQUENCE DESCRIPTION: SEQ ID NO: 25:

CAT ATG GAC GCC ACC ACC GGC GAC TTC ACG GCG CTG CAG AAG GCG GTG      48
    Met Asp Ala Thr Thr Gly Asp Phe Thr Ala Leu Gln Lys Ala Val
                490                 495                 500

AAG CAG ATG GCC ACC AAG GCG GGC ACT GAG GGC CTG GTG CAC GGC ATC      96
Lys Gln Met Ala Thr Lys Ala Gly Thr Glu Gly Leu Val His Gly Ile
            505                 510                 515

AAG AAC CCC GAC GTG CGC CAG CTG CTG ACC GAG ATC TTC ATG AAG GAC     144
Lys Asn Pro Asp Val Arg Gln Leu Leu Thr Glu Ile Phe Met Lys Asp
        520                 525                 530

CCG GAG CAG CAG GAG TTC ATG CAG GCG GTG CGC GAG GTG GCC GTC TCC     192
Pro Glu Gln Gln Glu Phe Met Gln Ala Val Arg Glu Val Ala Val Ser
535                 540                 545                 550

CTG CAG CCC GTG TTC GAG AAG CGC CCC GAG CTG CTG CCC ATC TTC AAG     240
Leu Gln Pro Val Phe Glu Lys Arg Pro Glu Leu Leu Pro Ile Phe Lys
                555                 560                 565

CAG ATC GTT GAG CCT GAG CGC GTG ATC ACC TTC CGC GTG TCC TGG CTG     288
Gln Ile Val Glu Pro Glu Arg Val Ile Thr Phe Arg Val Ser Trp Leu
                570                 575                 580

GAC GAC GCC GGC AAC CTG CAG GTC AAC CGC GGC TTC CGC GTG CAG TAC     336
Asp Asp Ala Gly Asn Leu Gln Val Asn Arg Gly Phe Arg Val Gln Tyr
            585                 590                 595

TCG TCC GCC ATC GGC CCC TAC AAG GGC GGC CTG CGC TTC CAC CCC TCC     384
Ser Ser Ala Ile Gly Pro Tyr Lys Gly Gly Leu Arg Phe His Pro Ser
        600                 605                 610

GTG AAC CTG TCC ATC ATG AAG TTC CTT GCC TTT GAG CAG ATC TTC AAG     432
Val Asn Leu Ser Ile Met Lys Phe Leu Ala Phe Glu Gln Ile Phe Lys
615                 620                 625                 630
```

```
AAC AGC CTG ACC ACC CTG CCC ATG GGC GGC GGC AAG GGC GGC TCC GAC        480
Asn Ser Leu Thr Thr Leu Pro Met Gly Gly Gly Lys Gly Gly Ser Asp
            635             640                 645

TTC GAC CCC AAG GGC AAG AGC GAC GCG GAG GTG ATG CGC TTC TGC CAG        528
Phe Asp Pro Lys Gly Lys Ser Asp Ala Glu Val Met Arg Phe Cys Gln
            650                 655             660

TCC TTC ATG ACC GAG CTG CAG CGC CAC ATC AGC TAC GTG CAG GAC GTG        576
Ser Phe Met Thr Glu Leu Gln Arg His Ile Ser Tyr Val Gln Asp Val
            665             670                 675

CCC GCC GGC GAC ATC GGC GTG GGC GCG CGC GAG ATT GGC TAC CTT TTC        624
Pro Ala Gly Asp Ile Gly Val Gly Ala Arg Glu Ile Gly Tyr Leu Phe
            680             685                 690

GGC CAG TAC AAG CGC ATC ACC AAG AAC TAC ACC GGC GTG CTG ACC CCG        672
Gly Gln Tyr Lys Arg Ile Thr Lys Asn Tyr Thr Gly Val Leu Thr Pro
695             700                 705             710

AAG GGC CAG GAG TAT GGC GGC TCC GAG ATC CGC CCC GAG GCC ACC GGC        720
Lys Gly Gln Glu Tyr Gly Gly Ser Glu Ile Arg Pro Glu Ala Thr Gly
                715             720                 725

TAC GGC GCC GTG CTG TTT GTG GAG AAC GTG CTG AAG GAC AAG GGC GAG        768
Tyr Gly Ala Val Leu Phe Val Glu Asn Val Leu Lys Asp Lys Gly Glu
            730                 735             740

AGC CTC AAG GGC AAG CGC TGC CTG GTG TCT GGC GCG GGC AAC GTG GCC        816
Ser Leu Lys Gly Lys Arg Cys Leu Val Ser Gly Ala Gly Asn Val Ala
            745             750                 755

CAG TAC TGC GCG GAG CTG CTG CTG GAG AAG GGC GCC ATC GTG CTG TCG        864
Gln Tyr Cys Ala Glu Leu Leu Leu Glu Lys Gly Ala Ile Val Leu Ser
760             765                 770

CTG TCC GAC TCC CAG GGC TAC GTG TAC GAG CCC AAC GGC TTC ACG CGC        912
Leu Ser Asp Ser Gln Gly Tyr Val Tyr Glu Pro Asn Gly Phe Thr Arg
775             780                 785             790

GAG CAG CTG CAG GCG GTG CAG GAC ATG AAG AAG AAG AAC AAC AGC GCC        960
Glu Gln Leu Gln Ala Val Gln Asp Met Lys Lys Lys Asn Asn Ser Ala
                795             800                 805

CGC ATC TCC GAG TAC AAG AGC GAC ACC GCC GTG TAT GTG GGC GAC CGC       1008
Arg Ile Ser Glu Tyr Lys Ser Asp Thr Ala Val Tyr Val Gly Asp Arg
            810                 815             820

CGC AAG CCT TGG GAG CTG GAC TGC CAG GTG GAC ATC GCC TTC CCC TGC       1056
Arg Lys Pro Trp Glu Leu Asp Cys Gln Val Asp Ile Ala Phe Pro Cys
            825                 830             835

GCC ACC CAG AAC GAG ATC GAT GAG CAC GAC GCC GAG CTG CTG ATC AAG       1104
Ala Thr Gln Asn Glu Ile Asp Glu His Asp Ala Glu Leu Leu Ile Lys
            840                 845             850

CAC GGC TGC CAG TAC GTG GTG GAG GGC GCC AAC ATG CCC TCC ACC AAC       1152
His Gly Cys Gln Tyr Val Val Glu Gly Ala Asn Met Pro Ser Thr Asn
855             860                 865             870

GAG GCC ATC CAC AAG TAC AAC AAG GCC GGC ATC ATC TAC TGC CCC GGC       1200
Glu Ala Ile His Lys Tyr Asn Lys Ala Gly Ile Ile Tyr Cys Pro Gly
            875                 880             885

AAG GCG GCC AAC GCC GGC GGC GTG GCG GTC AGC GGC CTG GAG ATG ACC       1248
Lys Ala Ala Asn Ala Gly Gly Val Ala Val Ser Gly Leu Glu Met Thr
            890                 895             900

CAG AAC CGC ATG AGC CTG AAC TGG ACT CGC GAG GAG GTT CGC GAC AAG       1296
Gln Asn Arg Met Ser Leu Asn Trp Thr Arg Glu Glu Val Arg Asp Lys
            905                 910             915

CTG GAG CGC ATC ATG AAG GAC ATC TAC GAC TCC GCC ATG GGG CCG TCC       1344
Leu Glu Arg Ile Met Lys Asp Ile Tyr Asp Ser Ala Met Gly Pro Ser
            920                 925             930

CGC AGA TAC AAT GTT GAC CTG GCT GCG GGC GCC AAC ATC GCG GGC TTC       1392
Arg Arg Tyr Asn Val Asp Leu Ala Ala Gly Ala Asn Ile Ala Gly Phe
```

```
                    935                 940                 945                 950
ACC AAG GTG GCT GAT GCC GTC AAG GCC CAG GGC GCT GTT TAAGCTGCCC                  1441
Thr Lys Val Ala Asp Ala Val Lys Ala Gln Gly Ala Val
                955                 960

AGGCCCAAGC CACGGCTCAC CGGCAATCCA AC                                              1473

(2) INFORMATION FOR SEQ ID NO: 26:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO: 26:

Met Asp Ala Thr Thr Gly Asp Phe Thr Ala Leu Gln Lys Ala Val Lys
 1               5                  10                  15

Gln Met Ala Thr Lys Ala Gly Thr Glu Gly Leu Val His Gly Ile Lys
            20                  25                  30

Asn Pro Asp Val Arg Gln Leu Leu Thr Glu Ile Phe Met Lys Asp Pro
        35                  40                  45

Glu Gln Gln Glu Phe Met Gln Ala Val Arg Glu Val Ala Val Ser Leu
    50                  55                  60

Gln Pro Val Phe Glu Lys Arg Pro Glu Leu Leu Pro Ile Phe Lys Gln
65                  70                  75                  80

Ile Val Glu Pro Glu Arg Val Ile Thr Phe Arg Val Ser Trp Leu Asp
                85                  90                  95

Asp Ala Gly Asn Leu Gln Val Asn Arg Gly Phe Arg Val Gln Tyr Ser
            100                 105                 110

Ser Ala Ile Gly Pro Tyr Lys Gly Gly Leu Arg Phe His Pro Ser Val
        115                 120                 125

Asn Leu Ser Ile Met Lys Phe Leu Ala Phe Glu Gln Ile Phe Lys Asn
    130                 135                 140

Ser Leu Thr Thr Leu Pro Met Gly Gly Gly Lys Gly Gly Ser Asp Phe
145                 150                 155                 160

Asp Pro Lys Gly Lys Ser Asp Ala Glu Val Met Arg Phe Cys Gln Ser
                165                 170                 175

Phe Met Thr Glu Leu Gln Arg His Ile Ser Tyr Val Gln Asp Val Pro
            180                 185                 190

Ala Gly Asp Ile Gly Val Gly Ala Arg Glu Ile Gly Tyr Leu Phe Gly
        195                 200                 205

Gln Tyr Lys Arg Ile Thr Lys Asn Tyr Thr Gly Val Leu Thr Pro Lys
    210                 215                 220

Gly Gln Glu Tyr Gly Gly Ser Glu Ile Arg Pro Glu Ala Thr Gly Tyr
225                 230                 235                 240

Gly Ala Val Leu Phe Val Glu Asn Val Leu Lys Asp Lys Gly Glu Ser
                245                 250                 255

Leu Lys Gly Lys Arg Cys Leu Val Ser Gly Ala Gly Asn Val Ala Gln
            260                 265                 270

Tyr Cys Ala Glu Leu Leu Leu Glu Lys Gly Ala Ile Val Leu Ser Leu
        275                 280                 285

Ser Asp Ser Gln Gly Tyr Val Tyr Glu Pro Asn Gly Phe Thr Arg Glu
    290                 295                 300

Gln Leu Gln Ala Val Gln Asp Met Lys Lys Lys Asn Asn Ser Ala Arg
305                 310                 315                 320
```

```
Ile Ser Glu Tyr Lys Ser Asp Thr Ala Val Tyr Val Gly Asp Arg Arg
            325                 330                 335
Lys Pro Trp Glu Leu Asp Cys Gln Val Asp Ile Ala Phe Pro Cys Ala
            340                 345                 350
Thr Gln Asn Glu Ile Asp Glu His Asp Ala Glu Leu Leu Ile Lys His
            355                 360                 365
Gly Cys Gln Tyr Val Val Glu Gly Ala Asn Met Pro Ser Thr Asn Glu
        370                 375                 380
Ala Ile His Lys Tyr Asn Lys Ala Gly Ile Ile Tyr Cys Pro Gly Lys
385                 390                 395                 400
Ala Ala Asn Ala Gly Gly Val Ala Val Ser Gly Leu Glu Met Thr Gln
                405                 410                 415
Asn Arg Met Ser Leu Asn Trp Thr Arg Glu Glu Val Arg Asp Lys Leu
            420                 425                 430
Glu Arg Ile Met Lys Asp Ile Tyr Asp Ser Ala Met Gly Pro Ser Arg
            435                 440                 445
Arg Tyr Asn Val Asp Leu Ala Ala Gly Ala Asn Ile Ala Gly Phe Thr
        450                 455                 460
Lys Val Ala Asp Ala Val Lys Ala Gln Gly Ala Val
465                 470                 475
```

POLYPEPTIDES AND POLYNUCLEOTIDES RELATING TO THE α- AND β-SUBUNITS OF GLUTAMATE DEHYDROGENASES AND METHODS OF USE

CROSS-REFERENCE TO A RELATED APPLICATION

This application is a continuation application of application Ser. No. 09/070,844, filed May 1, 1998 now abandoned which is a divisional application of application Ser. No. 08/725,596, filed Oct. 3, 1996 (now abandoned), which is a continuation-in-part of application Ser. No. 08/541,033, filed Oct. 6, 1995 (now U.S. Pat. No. 5,879,941, issued Mar. 9, 1999).

This invention was made with government support under USDA Competitive Grant Number 87-CRCR-1-2476. The government has certain rights in this invention.

BACKGROUND OF THE INVENTION

Inorganic nitrogen acquired by plants is ultimately converted to ammonium before being assimilated in organic nitrogen metabolism. One enzyme postulated to be involved in the assimilatory process is glutamate dehydrogenase (GDH), a group of ubiquitous enzymes found to be present in almost all organisms from microbes to higher plants and animals (Srivastava, H. S., R. P. Singh [1987] *Phytochem.* 26:597-610). GDH catalyses the reversible conversion of α-ketoglutarate to glutamate via a reductive amination that utilizes reduced β-nicotinamide adenine dinucleotide (NADH) or reduced β-nicotinamide adenine dinucleotide phosphate (NADPH) as a cofactor. The role of plant GDHs in the assimilation of ammonium into amino acids has been questioned since the discovery of the glutamine synthetase/glutamate synthase (GS/GOGAT) pathway that is believed to be the favored pathway for ammonium assimilation in higher plants (Miflin, B. J., P. J. Lea [1976] *Phytochem.* 15:873-885).

The primary objection to GDH playing a major role in plant nitrogen metabolism is its low affinity for ammonium that would require high intracellular ammonium concentrations to function anabolically. Early evidence indicated that GDH is a catabolic enzyme catalyzing the deamination of glutamate with only a partially anabolic function in synthesizing glutamate (Wallgrove, J. C., N. P. Hall, A. C. Kendall, [1987] *Plant Physiol.* 83:155-158). The physiological role of large amounts of GDH present in various plant tissues and organelles is still unclear, and possible conditions under which GDH may play a significant role in carbon and nitrogen metabolism have not been resolved.

The majority of plant GDHs characterized to date are localized in the mitochondria; however, a GDH species differing in several properties (e.g., cofactor specificity, $K_m$ values, organelle localization, thermal stability, among others) has been characterized from the chloroplast of a unicellular green alga *Chlorella sorokiniana*. *C. sorokiniana* cells have been shown to possess a constitutive, mitochondrial, tetrameric NAD-specific GDH (hereinafter designated "NAD-GDH") (Meredith, M. J., R. M. Gronostajski, R. R. Schmidt [1978] *Plant Physiol.* 61:967-974), and seven ammonium-inducible, chloroplast-localized, homo- and heterohexameric NADP-specific GDH isoenzymes (hereinafter designated "NADP-GDH")(Prunkard, D. E., N. F. Bascomb, R. W. Robinson, R. R. Schmidt [1986] *Plant Physiol.* 81:349-355; Bascomb, N. F., R. R. Schmidt [1987] *Plant Physiol.* 83:75-84). The seven chloroplastic NADP-GDH isoenzymes were shown to have different electrophoretic mobilities during native-PAGE, which can result from the formation of homo- and heterohexamers composed of varying ratios of α- and β-subunits (53.5 and 52.3 kilodaltons, respectively).

Chlorella cells cultured in 1 to 2 mM ammonium medium accumulate only the α-homohexamer (Bascomb and Schmidt, supra). The addition of higher ammonium concentrations (3.4 to 29 mM) to nitrate-cultured cells results in the accumulation of both α- and β-subunits in NADP-GDH holoenzymes (Prunkard et al., supra; Bascomb and Schmidt, supra; Bascomb, N. F., D. E. Prunkard, R. R. Schmidt [1987] *Plant Physiol.* 83:85-91). Prunkard et al. (Prunkard, D. E., N. F. Bascomb, N F, W. T. Molin, R. R. Schmidt [1986] *Plant Physiol.* 81:413-422) demonstrated that the NADP-GDH subunit ratio and isoenzyme pattern is influenced by both the carbon and nitrogen source as well as the light conditions under which cells are cultured.

The α- and β-NADP-GDH homohexamers purified from Chlorella cells have strikingly different ammonium $K_m$ values; however, the $K_m$ values for their other substrates are very similar. The α-homohexamer (composed of six identical α-subunits) that catalyzes the biosynthesis of glutamate is allosterically regulated by NADPH and possesses an unusually low $K_m$ for ammonium that ranges from 0.02 to 3.5 mM, depending on the NADPH concentration (Bascomb and Schmidt, supra). The $K_m$ value for ammonium of the α-homohexamer is the lowest reported ammonium $K_m$ for any plant GDH characterized to date. In contrast, the β-homohexamer (catabolic form) is a non-allosteric enzyme with an ammonium $K_m$ of approximately 75 mM. From these studies involving purified enzymes, it had been heretofore postulated that the heterohexamers have varying degrees of affinity for ammonium ranging between the $K_m$ values for the α- and β-homohexamers. Surprisingly, however, we have discovered that certain heterohexamers can have aminating:deaminating activity ratio which is greater than either the α- or β-homohexamers.

Although the α- and β-subunits have distinct in vivo turnover rates (Bascomb et al., supra) and the corresponding homohexamers have remarkably different ammonium $K_m$ values, the α- and β-subunits are derived from precursor proteins of nearly identical size (ca 58,000 Daltons) and were shown to have very similar peptide maps (Prunkard et al., supra; Bascomb and Schmidt, supra). Moreover, polyclonal antibodies prepared against the β-homohexamer are capable of immunoprecipitating all of the NADP-GDH isoenzymes—(Yeung, A. T., K. J. Turner, N. F. Bascomb, R. R. Schmidt [1981] *Anal. Biochem.* 10:216-228; Bascomb et al., supra), but do not crossreact with the mitochondrial NAD-GDH. In addition, previous research in this laboratory provided genomic cloning and southern blot evidence that indicated the *C. sorokiniana* genome possesses a single NADP-GDH structural gene (Cock, J. M., K. D. Kim, P. W. Miller, R. G. Hutson, R. R. Schmidt [1991] *Plant Mol. Biol.* 17:17-27).

The *C. sorokiniana* nuclear-encoded chloroplastic NADP-GDH isoenzymes are the only chloroplastic localized GDH sequences isolated and characterized from plants. Although the Chlorella GDH isoenzymes had been previously characterized, it has been discovered in the present invention that the two mature subunits arise via specific processing of two similar precursor proteins encoded by two mRNAs formed by alternative splicing of a pre-mRNA derived from a single nuclear gene. Furthermore, the identification of the cleavage site and amino-terminal peptide sequence of the mature functional GDH subunits had not been accomplished prior to the present invention.

BRIEF SUMMARY OF THE INVENTION

The present invention provides the isolation and characterization of two full-length cDNAs from mRNAs isolated from the unicellular green algae *Chlorella sorokiniana*. The two cDNAs encode the precursor proteins (α-precursor, 56.35 kD; β-precursor, 57.85 kD) that are processed to yield the mature α- and β-subunits (53.5 kD; 52.3 kD, respectively) that compose the active NADP-GDH hexameric isoenzymes. The present invention concerns a single NADP-GDH gene which is alternatively spliced to yield two mRNAs that encode two different chloroplast precursor proteins. These precursor proteins can then be processed to the mature α- and β-subunits of the NADP-GDH isoenzymes. Also described are useful fragments or mutants of the nucleotide and amino acid sequences which retain the disclosed activity or utility. For example, certain fragments of the amino acid sequences provided herein can be useful as transit peptides, providing the protein with the capability to enter and remain in certain cell compartments. The nucleotide sequences which are described herein, and fragments of those nucleotide sequences, can be useful, for example, as primers in amplification procedures or as probes to hybridize to complementary sequences of interest. The nucleotide and amino acid sequences and fragments thereof as described herein can also be useful as molecular weight markers or in identifying and conforming the relatedness of other nucleotide sequences, polypeptides, or isoenzymes which pertain to NADP-GDH.

The present invention further provides methods in which assimilation of inorganic nitrogen into organic nitrogen metabolism of higher plants can be altered by expressing GDH from *C. sorokiniana* or GDHs isolated from other organisms. The alteration of nitrogen assimilation can have the effect of increasing nitrogen assimilation which, as is well understood in the art, can affect the composition of the plant through an inverse effect on carbon metabolism, e.g., accumulation of carbohydrates. The subject invention also concerns DNA constructs for use in the described methods. The present invention includes the identification of the amino-terminal sequences of the α- and β-subunits which can assemble to form NADP-GDH isoenzymes, e.g., the native hexameric NADP-GDH found in *C. sorokiniana* chloroplasts. This precise molecular information can be employed to express NADP-GDH with the unique kinetic properties of the *C. sorokiniana* chloroplastic α- and β-NADP-GDH homohexamers. The present invention also provides recombinant cells or organisms, e.g., transgenic crops or plants which, by expressing the genes of the described polynucleotide sequences to produce corresponding polypeptides, can have an increased yield, improved ammonia assimilatory properties which can advantageously increase their tolerance of ammonia toxicity, improved osmotic stress tolerance, and improved composition of the crop or plant.

BRIEF DESCRIPTION OF THE SEQUENCES

Figure 1:
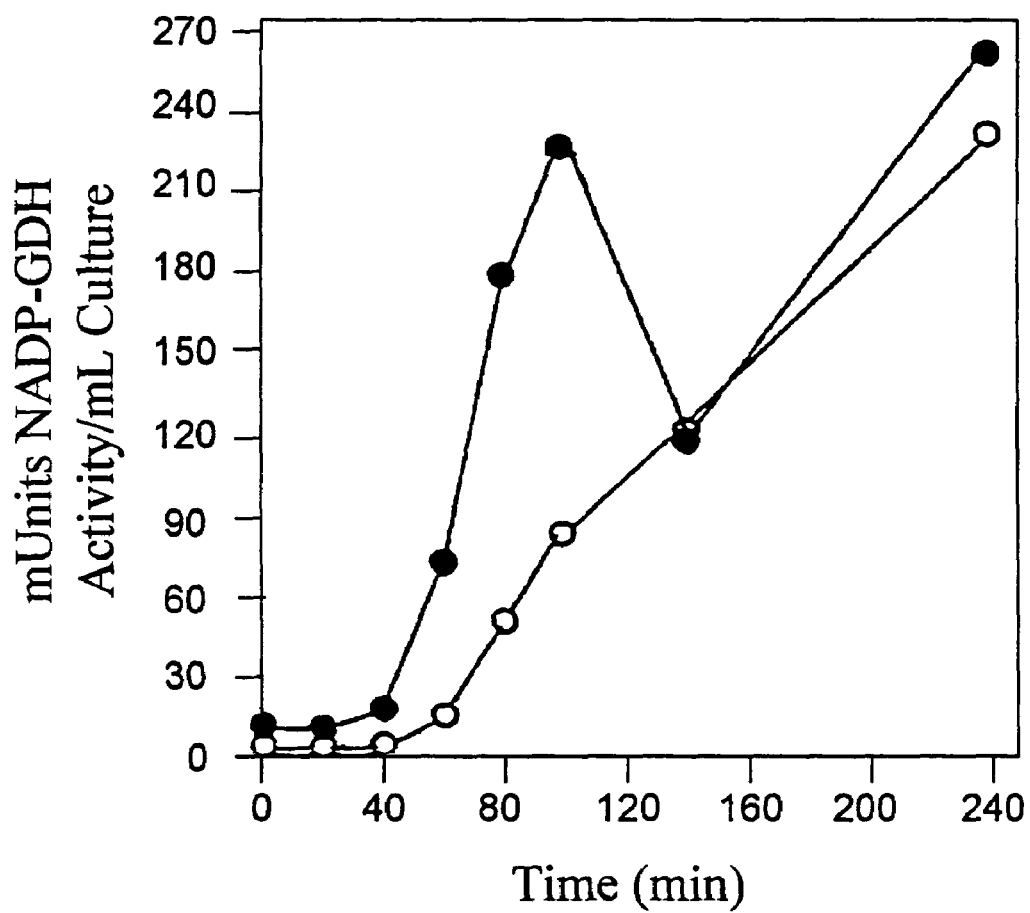
FIG. 1 shows a pattern of NADP-GDH activities in homogenates of synchronous *C. sorokiniana* cells cultured for 240 min in 29 mM ammonium medium in continuous light. Aliquots of clarified homogenates, from cell collected at various time intervals, were analyzed spectrophotometrically for both aminating (●) and deaminating (○) NADP-GDH activities.

SEQ ID NO.1 is the cDNA for the precursor-protein of the α-subunit of an NADP-specific glutamate dehydrogenase.

SEQ ID NO.2 is the deduced amino acid sequence of the polynucleotide of SEQ ID NO. 1.

SEQ ID NO.3 is the cDNA for the precursor-protein of the β-subunit of an NADP-specific glutamate dehydrogenase.

SEQ ID NO.4 is the deduced amino acid sequence of the polynucleotide of SEQ ID NO. 3.

SEQ ID NO.5 is the N-terminal sequence for the NADP-GDH α-subunit.

SEQ ID NO.6 is the N-terminal sequence for the NADP-GDH β-subunit.

SEQ ID NO.7 is the cDNA sequence in the clone designated pBGDc53.

SEQ ID NO.8 is a primer which hybridizes to the conserved region of NADP-GDH mRNAs.

SEQ ID NO.9 is a poly(dT) polynucleotide used as an adaptor primer according to the subject invention.

SEQ ID NO. 10 is a polynucleotide used as a primer according to the subject invention.

SEQ ID NO. 11 is a polynucleotide used as a primer according to the subject invention.

SEQ ID NO. 12 is a polynucleotide used as an adaptor primer according to the subject invention.

SEQ ID NO. 13 is the polynucleotide insert in the clone designated pRGDc 60.

SEQ ID NO. 14 is the polynucleotide insert in the clone designated pRGDc 61.

SEQ ID NO. 15 is the polynucleotide used as a primer according to the subject invention.

SEQ ID NO. 16 is the polynucleotide insert in a clone designated pGDc 63.

SEQ ID NO. 17 is the polynucleotide insert of a clone designated pGDc 64.

SEQ ID NO. 18 is the polynucleotide resulting from ligation of purified fragments of the inserts in the clones designated pBGDc 53 and pGDc 63, according to the subject invention.

SEQ ID NO. 19 is the polynucleotide resulting from ligation of purified inserts of the clones designated pGDc 64 and pBGDc 53.

SEQ ID NO. 20 is a polynucleotide used as a primer according to the subject invention.

SEQ ID NO. 21 is a polynucleotide used as a primer hybridizing to the 3' terminus of the template DNA according to the subject invention.

SEQ ID NO. 22 is a polynucleotide used as a primer according to the subject invention.

SEQ ID NO. 23 is the polynucleotide sequence (cDNA) of the processed, mature NADP-GDH α-subunit.

SEQ ID NO. 24 is the amino acid sequence of the processed, mature NADP-GDH α-subunit.

SEQ ID NO. 25 is the polynucleotide (cDNA) sequence of the processed, mature NADP-GDH β-subunit.

SEQ ID NO. 26 is the amino acid sequence of the processed, mature NADP-GDH β-subunit.

DETAILED DISCLOSURE OF THE INVENTION

The present invention provides heretofore undescribed polynucleotide sequences, for example, cDNAs for precursor-proteins of α- and β-subunits of an ammonium inducible, chloroplast-localized NADP-specific glutamate dehydrogenase (hereinafter NADP-GDH) from *Chlorella sorokiniana*. The nucleotide sequences for the precursor proteins of the α- and β-subunits that form NADP-GDH are shown in SEQ ID NOS. 1 and 3, respectively. The deduced amino acid sequences for the precursor-proteins of the α- and β-subunits of the NADP-GDH enzyme from *Chlorella sorokiniana* are shown in SEQ ID NOS. 2 and 4, respectively.

*E. coli* hosts comprising the subject cDNA inserts were deposited with the American Type Culture Collection (ATCC), 12301 Parklawn Drive, Rockville, Md. 20852 USA. The cultures were assigned the following accession numbers by the repository:

| Culture | Accession number | Deposit date |
|---|---|---|
| *E. coli* DH5α α-NADP-GDH SEQ No. 1 (+42 bp) | ATCC 69925 | Oct. 6, 1995 |
| *E. coli* DH5α β-NADP-GDH SEQ No. 1 (−42 bp) | ATCC 69926 | Oct. 6, 1995 |

The subject cultures have been deposited under conditions that assure that access to the culture(s) will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit(s), and in any case, for a period of at least 30 (thirty) years after the date of deposit or for the enforceable life of any patent which may issue disclosing the cultures. The depositor acknowledges the duty to replace the deposit(s) should the depository be unable to furnish a sample when requested, due to the condition of the deposit(s). All restrictions on the availability to the public of the subject culture deposits will be irrevocably removed upon the granting of a patent disclosing them.

Automated amino acid sequence analysis identifies 20 and 10 amino-terminal amino acid residues of the α- and β-subunits, respectively. Alignment of the α- and β-subunit peptide sequences reveals that the two subunits are identical with the exception of an 11-amino acid extension present in the larger α-subunit. Monoclonal antibodies raised against the α-subunit were shown to recognize the β-subunit providing further evidence that the two subunits are nearly identical. The identification of the unique α- and β-subunit processing sites within the precursor proteins provides the molecular mechanism to explain the different kinetic properties of the α- and β-NADP-GDH homohexameric isoenzymes.

The aforementioned data provide information applicable to genetically engineer plants with a specific GDH having favorable kinetic properties which can influence both carbon and nitrogen metabolism. Based on the high guanine/cytosine content the cDNAs are highly amenable for heterologous expression in higher plants. The introduction of either or both subunits with their chloroplast targeting sequences or with other organellar targeting sequences in heterologous plant systems can improve nitrogen assimilation and influence the carbon/nitrogen balance.

It has been discovered that chloroplast localization is related to, and can be dependent on, the N-terminus of the α- or β-precursor protein. Cleavage of the N-terminus of the precursors yields the mature proteins. Accordingly, the chloroplast transit peptide comprises a peptide which forms, or is an active fragment of, the N-terminus cleaved from the precursor protein. Peptides having similar or equivalent amino acid sequences, or that have a tertiary structure or conformation similar to these cleaved peptides can also function as transit peptides. The chloroplast-transit peptide comprises the active fragment of the N-terminal peptide cleaved from the α-precursor (a 40-mer) or the β-precursor (a 37-mer). The polynucleotide sequences encoding the chloroplast-transit peptides can be used by persons of ordinary skill in the art to produce chloroplast-transit peptides employed with the peptides described herein, or others known in the art.

Adding, removing, or replacing the chloroplast-transit peptide associated with a protein, e.g., the GDH enzyme, can be employed to localize the protein according to need, by means well known in the art. For example, localization of the enzyme in a chloroplast of a cell can be achieved by the insertion of a chloroplast-transit peptide onto an amino acid sequence lacking such a transit peptide. Species-specific chloroplast-transit peptides can be added or can replace those present to optimize insertion into the chloroplast of a desired species. In addition, localization inside the chloroplast of a protein expressed within the chloroplast can be achieved by direct transformation of the plastid with the polynucleotide sequences encoding an expressed protein. Similarly, removal of a chloroplast-transit peptide or production of a recombinant protein lacking the peptide can be utilized to sequester the protein in a cellular compartment other than the chloroplast.

Transformed plants expressing the α-homohexamer can be more tolerant to ammonia toxicity, assimilate ammonium more efficiently, and respond more rapidly to osmotic stress encountered in transiently saline soils by providing glutamate the precursor to the osmoprotectant proline. Expression of, for example, the β-homohexamer or GDH heterohexamers can be used to alter the rate of nitrogen assimilation, favoring accumulation of carbohydrates in fruits and other storage organs.

Unexpectedly, it was discovered that a hexamer comprising at least one α-subunit and at least one β-subunit, i.e., a heterohexamer, can have advantageous activity. Specifically, the aminating:deaminating activity ratio (i.e., biosynthetic capacity for synthesis of glutamate) of a chloroplastic NADP-GDH isozyme can be increased by incorporating both α- and β-subunits into the hexameric protein rather than using a homohexamer comprising only the α- or only the β-subunits. In one embodiment of the invention, it can be advantageous to co-express cDNAs encoding both types of subunits in the same plant at different rates/levels such that a particular ratio of α- and β-subunits is obtained in the heterohexamer. For example, we have discovered that an NADP-GDH heterohexamer having at least one of the subunits in the β-form is preferred for increasing aminating:deaminating activity ratio. A more preferred heterohexamer has 2-5 β-subunits. This differential rate of expression of the two cDNAs can be accomplished by placing them under the control of plant promoters with different strengths or under the same promoter that has been modified to generate different levels of expression. The use of this algal NADP-GDH isozyme system in plant biotechnology has advantages over NADP-GDHs from organisms, such as bacteria, that contain only a single form of the enzyme (i.e., no isozymes).

It is recognized that expression levels of certain recombinant proteins in transgenic plants can be improved via increased expression of stabilized mRNA transcripts; and that, conversely, detection of these stabilized RNA transcripts may be utilized to measure expression of translational product (protein). Low expression of protein RNA in plants and, therefore, of low protein expression, can be resolved through the use of an improved, synthetic gene specifying the desired protein from the gene source organism.

Thus, in one embodiment of the subject invention, bacteria and plants can be genetically engineered to attain desired expression levels of novel proteins having agricultural or otherwise commercial value. To provide genes having enhanced expression in plants, the DNA sequence of the gene can be modified to comprise codons preferred by highly expressed plant genes, to attain an A+T content in nucleotide base composition substantially that found in plants, and also preferably to form a plant initiation sequence, and to eliminate sequences that cause destabilization, inappropriate polyadenylation, degradation and termination of RNA and to avoid sequences that constitute secondary structure hairpins and RNA splice sites. For example, in synthetic genes, the codons used to specify a given amino acid can be selected with regard to the distribution frequency of codon usage employed in highly expressed plant genes to specify that amino acid. As is appreciated by those skilled in the art, the distribution frequency of codon usage utilized in the synthetic gene is a determinant of the level of expression.

For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell.

When synthesizing a gene for improved expression in a host cell it is desirable to design the gene such that its frequency of codon usage approaches the frequency of preferred codon usage of the host cell.

The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein this calculation includes unique codons (i.e., ATG and TGG). In general terms the overall average deviation of the codon usage of a synthetic gene from that of a host cell is calculated using the equation $$A = \sum_{n=1}^{Z} \frac{\frac{X_n - Y_n}{X_n} \times 100}{Z}$$

where $X_n$=frequency of usage for codon n in the host cell; $Y_n$=frequency of usage for codon n in the synthetic gene. Where n represents an individual codon that specifies an amino acid, the total number of codons is Z. The overall deviation of the frequency of codon usage, A, for all amino acids should preferably be less than about 25%, and more preferably less than about 10%. Hence, a gene can be designed such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C or G) nucleotide is the least preferred codon in dicots whereas the XTA codon is avoided in both monocots and dicots. Synthetic genes of this invention also preferably have CG and TA doublet avoidance indices closely approximating those of the chosen host plant. More preferably these indices deviate from that of the host by no more than about 10-15%.

Assembly of the NADP-GDH gene of this invention can be performed using standard technology known in the art. A structural gene designed for enhanced expression in plants of the specific embodiment can be enzymatically assembled within a DNA vector from chemically synthesized oligonucleotide duplex segments. The gene can then be introduced into a plant host cell and expressed by means known to the art. Preferably, the protein produced upon expression of the synthetic gene in plants is functionally equivalent to a native protein in having comparable or improved aminating/deaminating activity. According to the subject invention, functionally equivalent refers to identity or near identity of function. A synthetic gene product which has at least one property relating to its activity or function, which is the same or similar to a natural protein is considered functionally equivalent thereto.

Modifications in nucleotide sequence of the coding region can be made to alter the A+T content in DNA base composition of a synthetic gene to reflect that normally found in genes for highly expressed proteins native to the host cell. Preferably the A+T content of the synthetic gene is substantially equal to that of said genes for highly expressed proteins. In genes encoding highly expressed plant proteins, the A+T content is approximately 55%. It is preferred that the synthetic gene have an A+T content near this value, and not sufficiently high as to cause destabilization of RNA and, therefore, lower the protein expression levels. More preferably, the A+T content is no more than about 60% and most preferably is about 55%. Also, for ultimate expression in plants, the synthetic gene nucleotide sequence preferably can be modified to form a plant initiation sequence at the 5' end of the coding region. In addition, particular attention is preferably given to assure that unique restriction sites are placed in strategic positions to allow efficient assembly of oligonucleotide segments during construction of the synthetic gene and to facilitate subsequent nucleotide modification. As a result of these modifications in coding region of the native gene, the preferred synthetic gene is expressed in plants at an enhanced level when compared to that observed with natural structural genes.

It is known that the relative use of synonymous codons differs between the monocots and the dicots. In general, the most important factor in discriminating between monocot and dicot patterns of codon usage is the percentage G+C content of the degenerate third base. In monocots, 16 of 18 amino acids favor G+C in this position, while dicots only favor G+C in 7 of 18 amino acids.

For soybean and maize, the maize codon usage pattern resembles that of monocots in general, whereas the soybean codon usage pattern is almost identical to the general dicot pattern.

In designing a synthetic gene for expression in plants, it is preferred to eliminate sequences which interfere with the efficacy of gene expression.

A synthetic gene may be synthesized for other purposes in addition to that of achieving enhanced levels of expression. For example, in accordance with the subject invention, one of the nucleotide sequences encoding the α-subunit or the β-subunit of NADP-GDH can be modified such that the products are differentially expressed, favoring expression of one of the subunits. A result of such differential expression is a heterohexamer comprising more of one subunit than the other. Modification may encompass substitution of one or more, but not all, of the oligonucleotide segments used to construct the synthetic gene by a corresponding region of natural sequence. Preferably, differential expression of the nucleotide sequences encoding the α- and β-subunits of the NADP-GDH polypeptides can be employed to produce a heterohexamer having at least one β-subunit, more preferably two to five β-subunits, and most preferably three β-subunits.

The recombinant DNA molecule comprising a nucleotide sequence of the subject invention can be introduced into plant tissue by any means known to those skilled in the art. The technique used for a given plant species or specific type of plant tissue depends on the known successful techniques. As novel means are developed for the stable insertion of foreign genes into plant cells and for manipulating the modified cells, skilled artisans will be able to select from known means to achieve a desired result. Means for introducing recombinant DNA into plant tissue include, but are not limited to, direct DNA uptake (Paszkowski, J. et al. (1984) EMBO J. 3:2717), electroporation (Fromm, M. et al. (1985) Proc. Natl. Acad. Sci. USA 82:5824), microinjection (Crossway, A. et al. (1986) Mol. Gen. Genet. 202:179), or T-DNA mediated transfer from *Agrobacterium tumefaciens* to the plant tissue. There appears to be no fundamental limitation of T-DNA transformation to the natural host range of Agrobacterium. Successful T-DNA-mediated transformation of monocots (Hooykaas-Van Slogteren, G. et al. (1984) Nature 311:763), gymnosperms (Dandekar, A. et al. (1987) Biotechnology 5:587) and algae (Ausich, R., EPO application 108,580) has been reported. Representative T-DNA vector systems are described in the following references: An, G. et al. (1985) EMBO J. 4:277; Herrera-Estrella, L. et al. (1983) Nature 303:209; Herrera-Estrella, L. et al. (1983) EMBO J. 2:987; Herrera-Estrella, L. et al. (1985) in *Plant Genetic Engineering*, New York: Cambridge University Press, p. 63. Once introduced into the plant tissue, the expression of the structural gene may be assayed by any means known to the art, and expression may be measured as mRNA transcribed or as protein synthesized. Techniques are known for the in vitro culture of plant tissue, and in a number of cases, for regeneration in to whole plants. Procedures for transferring the introduced expression complex to commercially useful cultivars are known to those skilled in the art.

In one of its preferred embodiments the invention disclosed herein comprises expression in plant cells of an NADP-GDH gene under control of a plant expressible promoter, that is to say, by inserting the gene into T-DNA under control of a plant expressible promoter and introducing the T-DNA containing the insert into a plant cell using known means. Once plant cells expressing the gene under control of a plant expressible promoter are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques.

The introduction and expression of the NADP-GDH gene can be used to improve, e.g., increase, yields in a crop. Other uses of the invention, exploiting the properties of the genes introduced into plant species will be readily apparent to those skilled in the art.

Differences also exist between codon choice in plant nuclear genes and in chlorplasts. Chloroplasts differ from higher plants in that they encode only 30 tRNA species. Since chloroplasts have restricted their tRNA genes, the use of preferred codons by chloroplast-encoded proteins appears more extreme. However, a positive correlation has been reported between the level of isoaccepting tRNA for a given amino acid and the frequency with which this codon is used in the chloroplast genome (Pfitzinger et al. (1987) Nucl. Acids Res. 15:1377-1386. In general, the chloroplast codon profile more closely resembles that of unicellular organisms, with a strong bias towards the use of A+T in the degenerate third base.

Following are examples which illustrate procedures, including the best mode, for practicing the invention. These examples should not be construed as limiting. All percentages are by weight and all solvent mixture proportions are by volume unless otherwise noted.

EXAMPLES

Example 1

Kinetics of *C. sorokiniana* Chloroplast Glutamate Dehydrogenases

The chloroplastic glutamate dehydrogenase α- and β-isoenzymes used in the following experiments are naturally produced by an organism characterized as *Chlorella sorokiniana*.

*C. sorokiniana* culture conditions. For kinetic characterization in both the aminating and deaminating directions, the α- and β-holoenzymes were purified from cells that were accumulating only one form of homohexameric GDH isoenzyme.

The *C. sorokiniana* cells (UTEX-1230, University of Texas algal culture collection; 3B2NA, Robert R. Schmidt, University of Florida, Microbiology Cell Science Department) were cultured autotrophically as previously described by Prunkard et al., supra in a modified basal salts medium. The modified medium contained in mM concentration: $CaCl_2$, 0.34; $K_2SO_4$, 6.0; $KH_2PO_4$, 18.4; $MgCl_2$, 1.5; in μM concentration $CoCl_2$, 0.189; $CuCl_2$, 0.352; EDTA, 72; $FeCl_3$, 71.6; $H_3BO_3$, 38.8; $MnCl_2$, 10.1; $NH_4VO_4$, 0.20; $(NH_4)_6MO_7O_{24}$, 4.19; $NiCl_2$, 0.19; $SnCl_2$, 0.19; $ZnCl_2$, 0.734. The medium was supplemented with 1 mM $NH_4Cl$, 29 mM $NH_4Cl$, or 29 mM $KNO_3$ as a nitrogen source depending on the experimental conditions. The medium containing $NH_4Cl$ was adjusted to pH 7.4, and medium containing $KNO_3$ was adjusted to pH 6.8 with KOH after autoclaving. Cells were supplied with a 2% (v/v) $CO_2$-air mixture and light intensity sufficient to allow cell division into four progeny.

Purification of the NADP-GDH isoenzymes. For purification of the glutamate dehydrogenase α-isoenzyme, *C. sorokiniana* cells were cultured with continuous light in 29 mM ammonium medium in a 30 L Plexiglas chamber as previously described (Baker, A. L., R. R. Schmidt [1963] *Biochim. Biophys. Acta* 74:75-83). Cells were harvested at 4.0 $OD_{640}$ by centrifugation at 30,000 rpm through a Sharples centrifuge and washed two times in 10 mM Tris (pH 8.5 at 4° C.). Pelleted cells (130 g) were stored at −20° C. in 250 mL centrifuge bottles until use. Purification of NADP-GDH was accomplished using a modified procedure of Yeung et al., supra. Procedural modifications involved the substitution of Sephadex G-200 gel (Pharmacia) for G-150 gel in the gel-filtration column, and the addition of $NADP^+$ as a stabilizer to a final concentration of 0.1 mM to the gel-filtration buffer and all subsequent storage buffers. As a final modification, the $NADP^+$ affinity resin step was omitted and a preparative nondenaturing-PAGE step was substituted (Miller, P. W., W. D. Dunn, R. R. Schmidt [1994] *BioRad US/EG Bulletin* 1897).

The GDH deaminating enzyme assay solution was composed of 44 mM Tris, 20.4 mM glutamate, and 1.02 mM NADP+, pH 8.8. The aminating assay solution was composed of 50 mM Tris, 25 mM α-ketoglutarate, 0.357 mM NADPH, and 0.356 M $(NH_4)_2SO_4$, pH 7.4. One unit of enzyme activity was the amount of NADP-GDH required to reduce or to oxidize 1.0 μmol of $NADP^+$ or NADPH per minute at 38.5° C.

Sephadex G-200 column fractions possessing NADP-GDH activity were pooled and concentrated via Diaflow filtration. The soluble enzyme (68 mg) was protected from oxidation by the addition of DTT to a final concentration of 10 mM, and dialyzed for 30 minutes against 28.8 mM Tris, 192 mM glycine, 2 mM DTT (pH 8.4). The dialysate was clarified by centrifugation at 20,000 g for 10 minutes at 4° C. and was combined with 3 mL of 40% (w/v) sucrose and 1 mL of 0.02% bromophenol blue.

For preparative nondenaturing PAGE, a 3 cm tall 7% acrylamide (w/v, 28 acrylamide: 0.735 bis-acrylamide, pH 8.8) resolving gel, and a 2 cm tall 2% acrylamide (w/v, 1.6 acrylamide: 0.4 bis-acrylamide, pH 6.6) stacking gel were cast in the 28 mm ID gel tube of the Model 491 Prep Cell. All acrylamide stocks were pretreated with AG501-X8 mixed bed resin to remove any contaminating acrylic acid residue to prevent in vitro N-acylation of proteins during electrophoresis. The protein sample was electrophoresed at 15 mA constant power for 20 minutes and then for 3.5 hours at a constant power of 30 mA. Six milliliter fractions were collected and assayed for NADP-GDH deaminating activity and GDH containing fractions were pooled. The enzyme in the pooled fractions in 10 mM $KPO_4$ (pH 6.2), 0.1 mM $NADP^+$ was concentrated by Diaflow ultrafiltration to 1 mg/mL as determined by the method of Bradford, using BSA as a standard. The concentrated enzyme preparation was stored at −20° C. The purity of the preparation was determined by silver-staining to visualize proteins resolved by 10% (w/v) Tris-Tricine SDS-PAGE (Schagger, H., G. von Jagow [1987] *Anal. Biochem.* 166:368-379).

The NADP-GDH β-isoenzyme was purified from a mixture of cells cultured for 240 minutes in 1 mM ammonium medium (14 g), 90 minutes in 1 mM ammonium medium (6 g), and for 20, 40, 60, and 80 minutes in 29 mM ammonium medium (1 g/time point) according to Bascomb and Schmidt, supra. The NADP-GDH β-isoenzyme was partially purified using a scaled down modified procedure of Yeung et al., supra. The DEAE sephacel ion exchange columns (pH 7.4, and pH 6) were scaled down to a 40 mL bed volume and a 400 mL linear KCl gradient (0 to 0.4 M) was used to elute the proteins in 3 mL fractions. The pH 6 DEAE ion-exchange column fractions containing NADP-GDH were combined into two pools; corresponding to the leading and trailing halves of the NADP-GDH activity peak. The separate pooled fractions were dialyzed against 10 mM $KPO_4$ (pH 6.2), 2 mM DTT for 16 hours, and affinity purified using Type 3 $NADP^+$ affinity gel (Pharmacia) as previously described (Bascomb and Schmidt, supra). The NADP-GDH in the pooled fractions was concentrated via Diaflow ultrafiltration to 2 mg/ml protein, as determined by the method of Bradford (Bradford, M. M. [1976] *Anal. Biochem.* 72:248-254), and stored at 4° C. until further use. After resolution of the proteins by 8% (w/v) Tris-Tricine SDS-PAGE, the purity of the preparation was determined by silver staining.

Table 1 summarizes the $K_m$ values determined for both the α- and β-homohexameric isoenzyme aminating reaction.

TABLE 1

| GDH Isoform | Substrate | $K_m$ Value (mM) |
| --- | --- | --- |
| α-homohexamer | NADPH | 0.14 |
| | $NH_4^+$ | 0.02-3.5 |
| | α-ketoglutarate | 0.35* |
| β-homohexamer | NADPH | 0.14 |
| | $NH_4^+$ | 77 |
| | α-ketoglutarate | 12 |

*after Shatilov, V. R., W. L. Kretovich (1977) Mol. Cell Biochem. 15: 201-212.

Table 2 summarizes the $K_m$ values determine for both the α- and β-homohexameric isoenzyme deaminating reaction.

TABLE 2

| GDH Isoform | Substrate | $K_m$ Value (mM) |
| --- | --- | --- |
| α-homohexamer | $NADP^+$ | 0.04 |
| | Glutamate | 38.2 |
| β-homohexamer | NADP+ | 0.04 |
| | Glutamate | 32.3 |

Activity of the α-,β-heterohexamer. The aminating and deaminating activities of the mixture of native NADP-GDH isoenzymes (heterohexamers composed of varying ratios of the α- and β-subunits) were also measured with saturating levels of substrates throughout the 240 minute induction period (FIG. 1). The aminating and deaminating activities showed initial induction lags of 20 to 40 min, respectively. The aminating activity increased rapidly during the first 100 min, decreased sharply between 100 min and 140 min, and increased sharply once again between 140 min and 240 min. In contrast, the deaminating activity increased in almost a linear manner throughout the induction after the initial induction-lag.

Figure 2:
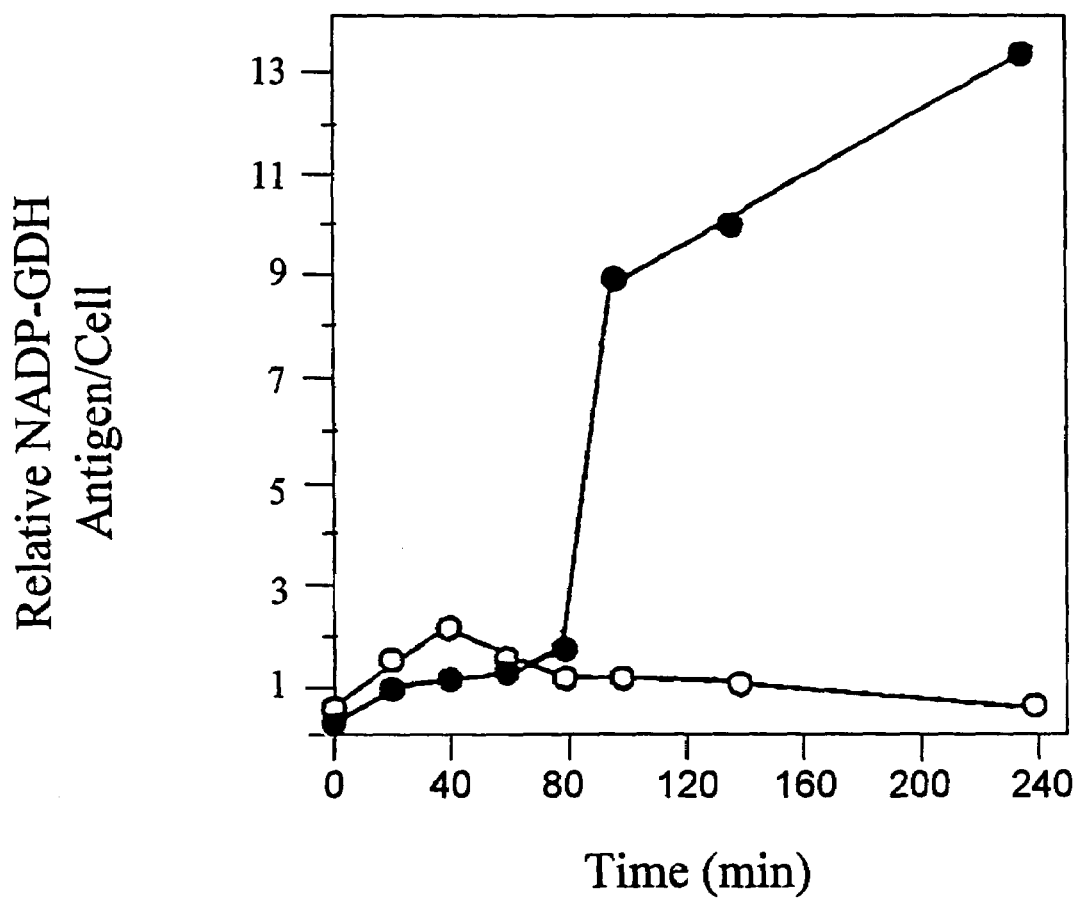
FIG. 2 shows patterns of accumulation of NADP-GDH antigens in illuminated cells cultured in 29 mM ammonium medium for 240 min. At zero time, ammonium was added to synchronous *C. sorokiniana* daughter cells and the culture was illuminated. Autoradiographs of Western blots were analyzed by laser densitometry to determine the relative levels of the NADP-GDH α-subunit (●) and β-subunit (○) throughout the 240 min induction period.

During the 240 min induction period in 29 mM ammonium medium, the patterns of accumulation of the *Chlorella sorokiniana* NADP-GDH α- and β-subunits in isoenzymes were also examined by use of a western blot immunodetection procedure following SDS polyacrylamide-gel electrophoresis (see FIG. 2). The NADP-GDH β-subunit was detected at $T_0$ and increased for the first 40 min followed by a gradual decrease through the remainder of the induction period. The α-subunit was first detected at 20 min. This subunit accumulated at a low rate for the first 80 min, showed a marked increase between 80 min and 100 min, and thereafter accumulated in a linear manner at a lower rate for the remainder of the induction period. The transition from the β-subunit being the prominent species to the α-subunit being prominent occurred between 60 and 80 min.

The aminating:deaminating activity ratio and the α:β subunit ratio were calculated to determine if changes in the subunit ratio in the mixture of NADP-GDH isoenzymes correlated with the predicted aminating:deaminating activity ratio during the time-course of the induction period (Table 3). Surprisingly, the highest aminating:deaminating ratio was observed at 60 min when the subunit ratio showed the β-subunit to be the prominent NADP-GDH antigen, whereas the α-subunit was the prominent form when the aminating: deaminating activity ratio was the lowest. This latter result was not predictable in advance.

Prior to this discovery, substrate kinetic studies of purified α- and β-homohexamers, the α-homohexamer, with its very high affinity for ammonium (relative to the β-homohexamer), was assumed to be the isoenzyme-form with the highest aminating activity (i.e., biosynthetic capacity for glutamate synthesis). The results suggested that the individual subunits would act independently with respect to their kinetic properties in homo- and heterohexamers.

Comparison of the aminating:deaminating activity ratio with the α:β subunit ratio throughout the 240 min induction in 29 mM ammonium medium revealed an unexpected correlation between the maxima in these ratios (Table 3).

Table 3. NADP-GDH aminating:deaminating activity and α-subunit:β-subunit ratios during ammonium induction period in C. sorokiniana cells.

TABLE 3

| Time (min) | Am:Deam Activity | α:β Subunit |
|---|---|---|
| 0 | 2.87 | 0.28 |
| 20 | 2.96 | 0.58 |
| 40 | 3.81 | 0.49 |
| 60 | 4.51 | 0.80 |
| 80 | 3.49 | 1.57 |
| 100 | 2.73 | 8.74 |
| 140 | 1.61 | 11.23 |
| 240 | 1.12 | 34.79 |

The peak in aminating:deaminating ratio occurred at 60 min at which time the β-subunit was the prominent but not exclusive antigen, whereas the α-subunit was prominent when the aminating:deaminating ratio was lowest. Interestingly, the aminating activity was highest when both subunits were present, suggesting that heterohexamer(s), formed by combination(s) of the α- and β-subunits, can have a higher aminating activity than a homohexamer. Based on the much lower $K_m$ of the purified α-homohexamer that the β-homohexamer for ammonium, it had been predicted earlier that the α-homohexamer would have a higher aminating activity than any heterohexamer composed of the two subunits (Bascomb and Schmidt, 1987).

Example 2—Sequencing of Polypeptides and Polynucleotides

Amino-terminal sequencing of the mature subunits. An aliquot of a preparation of purified NADP-GDH α-subunit (120 pmol) and a partially purified preparation of NADP-GDH α-subunit (80 pmol) and β-subunit (50 pmol) were resolved by 8% (w/v) Tris-Tricine SDS-PAGE and electroblotted to a PVDF membrane (Imobilon-P$^{SQ}$, Millipore) as described by Plough et al. (Plough, M., A. L. Jensen, V. Barkholt [1989] Anal. Biochem. 181:33-39). To prevent in vitro acylation of the protein amino-terminal residues, all polyacrylamide solutions used in PAGE were treated with AG501-X8 mixed bed resin to remove contaminating acrylic acid. An Applied Biosystems, Inc. model 470A gas phase sequencer was utilized for automated Edman degradation amino sequence analysis. The PTH-aa derivatives were identified by RP-HPLC. Protein sequence analysis of the electroblotted proteins was provided by the Interdisciplinary Center for Biotechnology Research Protein Chemistry Core facility at the University of Florida.

The following N-terminal sequence was determined for the α-subunit: AVSLEEQISAMDATTGDFTA (SEQ ID NO. 5). The following N-terminal sequence was determined for the β-subunit: DATTGDFTAL (SEQ ID NO. 6). These sequences are identical to the ORF identified in the two NADP-GDH cDNAs and indicate the positions of the internal cleavage sites utilized to remove the chloroplast targeting peptide sequences. The chloroplast targeting peptide sequences (or chloroplast-transit peptides) can be useful for cell compartment localization with these and other amino acid sequences. The polynucleotides encoding the chloroplast-transit peptides can be used with other polynucleotide sequences to encode chloroplast-transit peptides.

cDNA isolation and sequencing. A pellet of C. sorokiniana cells stored at −70° C. was resuspended 1 to 10 (w/v) in RNA breakage buffer: 0.1M Tris (pH 8.5), 0.4M LiCl, 10 mM EGTA, 5 mM EDTA, 100 units/mL sodium heparin (Sigma, 100 units/mg), and 1 mM aurintricarboxylic acid (Sigma). The cell suspension was centrifuged at 7000 g for 5 minutes at 4° C. and the supernatant was discarded. The cell pellet was resuspended 1 to 10 (w/v) in RNA breakage buffer and ruptured by passage through a French pressure cell at 20,000 p.s.i. The cell homogenate was collected in a disposable 50 mL conical tube containing 0.05 times volume 20% (w/v) SDS, 0.05 times volume 0.5 M EDTA (pH 8), 200 µg/mL proteinase K, and allowed to incubate at room temperature for 15 minutes. One-half volume of TE buffer (Tris 10 mM:EDTA 1 mM, pH 8.0) equilibrated phenol was added to the homogenate and after a 3 minutes incubation a one-half volume of chloroform:isoamylalcohol (24:1,v/v) was added and mixed for 10 minutes on a wrist action shaker. The extracted homogenate was transferred to a 30 mL siliconized corex tube and centrifuged at 1000 g for 10 minutes at 4° C. The upper aqueous phase was removed and repeatedly extracted with an equal volume of chloroform: isoamyl-alcohol (24:1, v/v), as described above, until the aqueous interface was clear. After the final extraction, the aqueous phase was combined with an equal volume of 2×LiCl-Urea buffer (4 M LiCl, 4 M urea, 2 mM EDTA, 1 mM aurintricarboxylic acid; Sigma) and the RNA was precipitated on ice for 16 hours at 4° C. The RNA precipitate was centrifuged at 4000 g for 20 minutes at 4° C. and the resulting pellet was rinsed once with 1× LiCl-Urea buffer and centrifuged again to pellet the RNA. The RNA pellet was solubilized in TE (pH 7.5) and an aliquot was quantified spectrophotometrically at 260 nm. After quantitation, the mRNA fraction was isolated from total cellular RNA using an oligo(dT) spin column kit. Poly(A)$^+$ RNA (50 µg) from each preparation was combined and utilized for the commercial production of a custom λUni-ZAP XR C. sorokiniana cDNA library (Stratagene Cloning Systems, Palo Alto, Calif.).

The amplified λZAP library, containing 2×10$^{10}$ pfu/mL, was plated on twenty 150 mm petri plates at 50,000 pfu per plate for a total of 1×10⁶ pfu screened. The phage plaques were absorbed to duplicate Hybond-N 132 mm circular membranes and treated according to the plaque blotting protocol of Amersham (1985, Amersham International plc, Arlington Heights, Ill.). Membranes were prehybridized in a common container in 200 mL of 2× PIPES (0.8 M NaCl, 20 mM PIPES, pH 6.5), 50% (w/v) formamide, 0.5% (w/v) SDS, 100 µg/mL denatured sheared salmon sperm DNA at 40° C. Blocked membranes were hybridized at 42° C. in ten heat-sealable bags (four membranes/bag) in prehybridization buffer containing 1×10⁶ cpm/membrane of a ³²P-labeled NADP-GDH 242 bp HCR cDNA probe on a lab rocker. The membranes were washed three times in 200 mL of 0.1×SSC, 0.1% (w/v) SDS for 20 minutes per wash at 50° C. Duplicate membranes were wrapped in plastic wrap and exposed to Kodak X-Omat AR film at −70° C. for 28 hours. Putative NADP-GDH cDNA plaques, detected on duplicate membranes, were cored from the plate and plaque purified by secondary and tertiary screenings with the 242 bp conserved region probe. Putative NADP-GDH cDNA phage clones, selected in the primary screening, were combined and screened a second time with a ³²P-labeled 130 bp Eco RI/Bgl II cDNA fragment isolated from the 5' terminus of the most complete 5' end NADP-GDH cDNA clone. Ten plaque pure NADP-GDH clones were subcloned in pBluescript KS⁺ (Stratagene) and transformed into *E. coli* DH5α F' (Bethesda Research Laboratories, BRL) via an in vivo excision protocol provided by Stratagene. All plasmid isolations were performed as described by Kraft et al. (Kraft, R., J. Tardiff, K. S. Krauter, L. A. Leinwand [1988] *Biotechniques* 6:544-547). Sequence analysis revealed all ten clones were identical at their 3'-termini and differed by varying degrees of truncation at their 5'-termini. The longest cDNA clone with a complete 3'-terminus designated pBGDc53 (SEQ ID NO. 7) was not long enough to encode either subunit; therefore, the 5'-terminal sequences were determined by RACE PCR.

The 5'-terminal NADP-GDH cDNA sequences were cloned using a modified anchored PCR procedure for the rapid amplification of cDNA ends (Frohman, M. A. [1990] In D. H. Gelford, J. J. Snincky, T. J. White, eds, *PCR Protocols*, Academic Press, San Diego, Calif., pp 28-38; Jain, R., R. H. Gorner, J. J. Murtagh [1992] *Biotechniques* 12:58-59). A mixture of poly(A)⁺ RNA, used in the synthesis of the λZAP library, was utilized to clone the 5' end of the NADP-GDH mRNA. One hundred nanograms of the mRNA mixture were combined with 10 ng of a gene-specific primer (5'-CTCAAAGGCAAGGAACTTCATG-3', SEQ ID NO. 8), designed to hybridize to the conserved region of NADP-GDH mRNAs, heated for 5 minutes, and chilled on ice. First strand DNA synthesis was performed using Superscript™ reverse transcriptase (BRL) according to the supplier's protocol. The terminated reverse transcription reaction was treated with one unit of ribonuclease H for 20 minutes at 37° C., 5 minutes at 95° C., and extracted once with chloroform:isoamyl alcohol (24:1, v/v). Excess primers and dNTPs were removed by centrifugation at 2000 rpm through an Ultrafree-MC filterfuge tube (30,000 MW cutoff, Millipore) and the retentate was concentrated to 10 µl on a Savant Speedvac. The first-strand synthesis products were combined with 10 µL of tailing mix (1× tailing buffer [Promega Corp.], 0.4 mM dATP, 10 units terminal deoxytransferase) and incubated at 37° C. for 10 minutes. The reaction mixture was heated to 95° C. for 5 minutes, diluted to 0.5 mL with TE (pH 8), and utilized as a cDNA pool. A mixture of 5 µL of the cDNA pool, 5 µL of Vent™ polymerase 10× buffer (New England Biolabs), 200 µM of each dNTP, 25 pmol of a gene specific primer (SEQ ID NO. 8), 5 pmol of the poly(dT) adaptor primer (5'-GGGTCGACATTCTAGACAGAATTCGTGGATCC(T)₁₈-3'; SEQ ID NO. 9), 0.2 units Perfectmatch™ DNA polymerase enhancer (Stratagene), and 1 unit of Vent™ polymerase (NEB) in 50 µL was amplified according to Jain et al., supra. The PCR products were purified away from the excess primers by centrifugation at 2,000 rpm through an Ultrafree-MC unit. The retentate was collected and subjected to two more rounds of amplification using a new nested gene specific primer at each step (5'-GGACGAGTACTGCACGC-3', SEQ ID NO. 10; 5'-GATCTCGGTCAGCAGCTG-3', SEQ ID NO. 11, respectively) and an adaptor primer (5'-GGGTCGACATTCTAGACAGAA-3'; SEQ ID NO. 12). PCR amplifications were performed in a Model 480 thermocycler (Perkin-Elmer Cetus), and all custom oligonucleotides were synthesized by the ICBR DNA synthesis facility, University of Florida. The standard PCR reaction mixture consisted of 10 µL of 10× Vent™ polymerase buffer, 100 µM of each dNTP, 0.4 units of Perfectmatch™, 50 pmol of each primer, 1 unit Vent™ DNA polymerase in a 100 µl reaction volume. The 5' RACE-PCR products were gel purified, subcloned into the SmaI site of pUC 18, and transformed into *E. coli* DH5α for further characterization. RACE PCR identified two 5' cDNA clones, which overlapped with the previously identified pBGDc 53 clone, that differed by a 42 nt insert identified in one clone designated pRGDc 60 (SEQ ID NO. 13) and lacking in the second cDNA designated pRGDc 61 (SEQ ID NO. 14).

Two additional cDNA clones lacking the RACE PCR polylinker, but possessing the complete 5'-termini corresponding to pRGDc 60 and 61 were constructed by RT-PCR amplification from mRNA using reaction conditions as described above and the gene specific primer pair (5'-CTTTCTGCTCGCCCTCTC-3', SEQ ID NO. 15, and SEQ ID NO. 11, above). The two PCR products were cloned into the SmaI site of pBluescript SK+ (Stratagene) and trans-formed into *E. coli* DH5α for further characterization. The cDNA clone that possessed the 42 nt insert was designated pGDc 63 (SEQ ID NO. 16) whereas the cDNA lacking the insert was designated pGDc 64 (SEQ ID NO. 17).

Full-length NADP-GDH cDNAs were constructed by restriction endonuclease treating pGDc 63 and 64 with EcoRI/ApaLI and gel purifying the resultant (264 bp; 222 bp, respectively) fragments. The gel purified fragments were ligated to a purified ApaLI/XhoI restriction fragment of pBGDc 53 and the full length ligation products (SEQ ID NO. 18; SEQ ID NO. 19) were gel agarose gel purified and utilized in subsequent PCR reactions.

Expression of α- and β-homohexamers in *E. coli*. Using the gel purified product (SEQ ID NO. 18), PCR mutagenesis was performed to remove the chloroplast targeting signal from the full-length cDNA and yield cDNAs encoding specifically the mature α- and β-subunits. Two sets of primer pairs were designed to synthesize α- and β-GDH subunit genes.

The following primer was designed to add a methionine to the amino terminus of the processed mature α-NADP-GDH subunit (alanine-41) to allow translation initiation and to generate a 5'NdeI site for subcloning purposes: 5'-CATATGGC-CGTCTCGCTGGAGGAG-3' (SEQ ID NO. 20). The following second primer was designed to hybridize to the 3' terminus of the template DNA at a position 20 nt 3' of the endogenous TAA termination codon: 5'-GTTGGATTGCCG-GTGAGCC-3' (SEQ ID NO. 21).

The following primer was designed to add a methionine to the amino terminus of the processed mature β-subunit (aspartate-38) to allow translation initiation and to generate a 5' NdeI site for subcloning purposes: 5'-CATATGGACGC-CACCACCGGC-3' (SEQ ID NO. 22). The second 3' primer used in the PCR amplification was the 3'-terminus primer (SEQ ID NO. 21) described for the α-subunit amplification.

PCR cycling conditions were as follows: 95° C., 50 seconds; 64° C., 1 minute; 72° C., 1 minute 35 seconds (30 cycles). Primer, dNTP, Vent polymerase, and other reaction component concentrations were as previously described. The 1506 bp α-NADP-GDH subunit gene (SEQ ID NO. 23) and 1473 bp P-GDH subunit gene (SEQ ID NO. 25) PCR products were gel purified and given a 3' adenine nucleotide overhang by incubating the purified fragment with 100 µM dATP and Taq polymerase for 15 minutes at 72° C. The modified PCR products were cloned into the PCRII T/A cloning vector (Invitrogen) and transformed into competent E. coli cells. Clones bearing the inserts were selected by blue-white screening, plasmid purified, and digested with NdeI/BamHI to select for the proper orientation in the cloning vector. The selected plasmids were restricted with NdeI and BamHI (BamHI site provided by vector) and directionally cloned under the control of the IPTG inducible T7 polymerase promoter of pET 11a and pET 15b bacterial expression vectors (Novagen) linearized with NdeI/BamHI, and transformed into DH5α. Transformants were screened by NdeI/BamHI restriction analysis and clones possessing the properly oriented α- and β-subunit cDNAs (SEQ ID NO. 23; SEQ ID NO. 25) were selected, plasmid purified, and transformed into E. coli BL21(DE3) for protein expression purposes.

E. coli BL21(DE3) cells transformed with pET 11a-α-cDNA and pET 11a-β-cDNA constructs were induced with 100 mM IPTG for 1 hour. Protein extracts from the induced cells were tested by enzyme analysis for NADP-GDH activity, and the denatured proteins were resolved by SDS gel electrophoresis, and visualized by coomassie staining. The proteins expressed by the mature α-subunit cDNA (SEQ ID NO. 23) and the β-subunit cDNA (SEQ ID NO. 25) have the amino acid sequences shown in SEQ ID NO. 24 (α-subunit) and SEQ ID NO. 26 (β-subunit). The recombinant GDH subunits were verified by crossreactivity with rabbit anti-Chlorella NADP-GDH antibodies.

Under conditions not optimized for maximal induction, the E. coli cells, possessing the α- and β-GDH cDNAs and induced with IPTG, showed 60- and 7,000-fold increases in NADP-GDH activity relative to uninduced controls, respectively. The recombinant α- and β-NADP-GDHs are currently being analyzed to verify kinetic and biochemical properties.

The over-expression and assembly of the C. sorokiniana chloroplastic GDHs into active enzymes provides proof that the DNA constructs engineered via PCR are transcribed and translated into authentic proteins. The aforementioned constructs were then utilized for cytosolic expression of the algal GDHs in transgenic plants.

Transformation of plants. A method for producing genetically transformed plants that express increased levels of a specific GDH requires the introduction of a double-stranded recombinant DNA molecule into the nuclear genome of a plant cell. The DNA molecule must (1) contain a structural DNA for the GDH enzyme being introduced into the plant cell; (2) possess a promoter which functions in plants to regulate the production of an RNA sequence in a constitutive or tissue-specific manner by RNA polymerase enzyme; and (3) have a 3'-untranslated region which functions to cause transcriptional termination and the addition of polyadenylated nucleotides to the 3' end of the RNA. The resulting primary RNA molecule is subsequently processed in the nucleus, a process which involves the removal of intronic sequences and the addition of polyadenylate nucleotides to the 3' end of the mRNA.

Promoters which are useful in the present invention are those that can initiate transcription in a constitutive manner or in a tissue-specific manner where glutamate production or catabolism is desired. An example of a useful constitutive promoter is the CaMV enhanced 35S promoter that directs the synthesis of RNA in a tissue independent manner. Promoters which cause production of GDH specifically in seeds, stems, roots, leaves, or specific cell types in these tissues are useful in the present invention. For example, the seed-specific Phaseolin promoter is one such tissue-specific promoter. Thus native promoters for maize, wheat, barley, and rice may be obtained and used in the present invention as well as heterologous promoters from other organisms shown to function in a constitutive/tissue-specific manner.

Introns. Generally, optimal expression in monocotyledonous plants is obtained when an intron sequence is inserted between the promoter sequence and the structural gene sequence. An example of such an intron sequence is the HSP 70 intron described in WO 93/19189.

Polyadenylation signal. The DNA constructs of the present invention can possess a 3' untranslated region which functions in plants to direct the addition of polyadenylate nucleotides to the 3' end of the RNA. An example of a suitable 3' untranslated region is the polyadenylation signal of the Agrobacterium tumor inducing plasmid, i.e., nopaline synthatase (NOS) gene.

Plastid targeting sequence. The DNA constructs of the present invention can optionally contain a plastid targeting sequence. The plastid targeting sequence directs the import of the protein into the plastid, and is removed during importation. The plastid targeting sequence can be, but is not limited to, the native chloroplast targeting peptide (CTP) identified in the C. sorokiniana NADP-GDH full-length cDNAs which encode the precursor proteins. A fusion of a selected plastid targeting sequence and the mature α- and β-NADP-GDH subunit sequences can be made by standard procedures and used in the present invention. GDH subunits lacking these targeting sequences are typically found in the cytoplasm of the cell. Such a cytosolic localized enzyme can be useful in capturing ammonium or glutamate compartmentalized in the cytosol of the cell.

GDH gene sources. The GDH gene used in the DNA constructs of the present invention can be any GDH gene. It is not limited to the C. sorokiniana GDH genes described above, although they are preferred. For example, a GDH gene from bacteria or fungi can be used. The examples provided use the α- and β-GDH genes of C. sorokiniana, but should not be interpreted in any way to limit the scope of the present invention. Individuals skilled in the art will recognize that various other genes as well as alterations can be made to genes and methods described herein while not departing from the spirit and scope of the present invention. For example, mutagenesis and routine screening can be implemented by techniques well known in the art to produce mutant variants that lack regulation by the cofactor NADPH.

Transient expression in maize protoplasts. In order to test the expression of the C. sorokiniana GDH subunits and their assembly into active enzymes in Zea mays cells, vectors were constructed to contain the CaMV E35S promoter, the coding sequence for the mature α-subunit (pMON21904) or β-subunit (pMON21905), the NOS 3'-untranslated polyadenylation region, and kanamycin resistance for selection in E. coli. The α- and β-subunit genes were isolated as a XbaI-EcoRI fragment from pET 11 a-α-cDNA and pET 11a-β-cDNA, respectively. The GDH genes were ligated into the XbaI-EcoRI E35S promoter, NOS 3', kanamycin resistance bearing region of pMON22072 to give pMON21904, and pMON21905. The DNA constructs were electroporated into maize and wheat protoplast according to the method of Sheen et al. (*The Plant Cell Vol.* 3, 225-245).

Analysis of transformed maize protoplasts. Pelleted protoplast samples transformed with pMON21904 (α-subunit), pMON21905 (β-subunit), pMON21709 (kanamycin negative control DNA), and no DNA were thawed in 0.2 mL of GDH cell breakage buffer (Yeung et al., supra) on ice. The cells in each suspension were homogenized twice for 30 seconds, chilled on ice, and clarified at 14,000 rpm for 10 minutes. Cell extracts were assayed in the deaminating direction at 38.5° C. according to Yeung et al., supra. Total protein content of the cell extracts was determined using the BioRad microprotein assay according to the manufacturer's protocol. Activities were normalized against total protein content for comparisons among different preparations. One unit of GDH activity is defined as the amount of enzyme necessary to reduce 1 μmol of NADP per minute at 38.5° C.

Protoplasts transformed with the control vector pMON21709 (n=3) or protoplasts not transformed (n=3) had no detectable NADP-GDH activity. Protoplasts transformed with pMON21904 (n=3) expressed 3.31 Units $mg^{-1}$ protein of GDH activity, whereas pMON21905 transformed protoplasts (n=3) 1.96 Units $mg^{-1}$ protein.

The high level of activity observed for the protoplasts transformed with the cytoplasmic expressed *C. sorokiniana* α- and β-NADP-GDH genes provides evidence that the GDH subunits are expressed in heterologous plant systems. Additionally, expression levels demonstrate that the subunits are assembled into active enzymes. Generally, it would be readily apparent to persons of ordinary skill in the art that superfluous sequences added to the described sequences, or fragments of the nucleotide or amino acid sequences described herein, which result in polynucleotides or amino acid sequences that function similarly or equivalently to the sequences expressly described herein, should also be considered part of this invention. They can easily and routinely be produced by techniques well known in the art, for example, by time-controlled Bal31 exonuclease digestion of the full-length DNA, followed by expression of the resulting fragments and routine screening of the expression products as described in the foregoing example. In addition, it would be readily accepted by ordinarily skilled artisans that the function, property, or utility of the described sequences can be negatived by inserting mutations into the sequences by standard techniques and procedures. These mutations which, by implication, effectively serve to remove the property or function inherent in the sequences as described are hereby expressly included as part of the invention. For example, a clear distinction between the α- and β-subunits of the *C. sorokiniana* is the 11-amino acid polypeptide sequence at the N-terminus of the α-subunit, but absent in the β-subunit. This sequence can affect the affinity, specificity, and modulation of ammonium compounds by the enzyme. Therefore, it would be apparent that inserting (if absent) or removing (if present) the appropriate sequence, or its functional equivalent, to effect a difference in certain characteristics of other GDH genes, or their products, would be easily carried out by those persons.

It should also be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A method for increasing or decreasing nitrogen metabolism in plant cells, said method comprising the steps of transforming a plant cell with a recombinant polynucleotide comprising a polynucleotide sequence encoding a polypeptide having glutamate dehydrogenase activity, and culturing said cell whereby descendant cells are produced which comprise said polynucleotide sequence and express said polynucleotide sequence, whereby nitrogen metabolism is increased or decreased as compared to nitrogen metabolism of untransformed plant cells; wherein said polynucleotide sequence is operably linked to a polynucleotide encoding a chloroplast transit peptide, and wherein the chloroplast transit peptide comprises SEQ ID NO: 5 or SEQ ID NO: 6, or a fragment thereof of sufficient length to exhibit chloroplast transit activity.

2. A method for increasing or decreasing nitrogen metabolism in plant cells, said method comprising the steps of transforming a plant cell with a recombinant polynucleotide comprising a polynucleotide sequence encoding a polypeptide having glutamate dehydrogenase activity, and culturing said cell whereby descendant cells are produced which comprise said polynucleotide sequence and express said polynucleotide sequence, whereby nitrogen metabolism is increased or decreased as compared to nitrogen metabolism of untransformed plant cells, wherein said polypeptide is selected from the group consisting of SEQ ID NO: 2, SEQ ID NO:4, SEQ ID NO:24, SEQ ID NO:26, and fragments of any of the foregoing of sufficient length to exhibit a-GDH or 13-GDH activity.

3. A method of increasing biomass, increasing total protein in seeds and plants, increasing total carbon/nitrogen level, increasing grain density, or increasing plant yield comprising culturing a plant comprising transgenic cells that comprise a polynucleotide encoding a polypeptide having glutamate dehydrogenase activity under conditions where said polynucleotide is expressed in said cells, whereby biomass is increased, total protein in seeds and plants is increased, total carbon/nitrogen level is increased, grain density is increased, or plant yield is increased, as compared to an untransformed plant; wherein said polypeptide is selected from the group consisting of SEQ ID NO: 2, SEQ ID NO: 4, SEQ ID NO: 24, SEQ ID NO: 26, and fragments thereof having glutamate dehydrogenase activity.

4. Transgenic plant cells comprising an expression cassette having:
- a tissue specific transcription initiation region functional in said transgenic plant cells;
- a DNA sequence that encodes a bacterial NADP-GDH enzyme in said transgenic plant cells; and
- a transcription termination region functional in said transgenic plant cells; wherein said expression cassette imparts increased yield to a transgenic plant resulting from the transgenic plant cells relative to wild-type plants resulting from wild-type plant cells.

5. The transgenic plant cells according to claim 4, further comprising a chloroplast transit peptide adapted to target the NADP-GDH enzyme to the chloroplasts.

6. The transgenic plant cells according to claim 4, wherein said transcription initiation region is seed specific.

* * * * *

UNITED STATES PATENT AND TRADEMARK OFFICE
CERTIFICATE OF CORRECTION

PATENT NO. : 7,485,771 B2 Page 1 of 1
APPLICATION NO. : 10/627886
DATED : February 3, 2009
INVENTOR(S) : Robert R. Schmidt and Philip Miller It is certified that error appears in the above-identified patent and that said Letters Patent is hereby corrected as shown below:

Column 16,
Line 45, "gel agarose gel purified" should read --gel agarose, gel purified--.

Column 17,
Line 8, "P-GDH" should read --β-GDH--.

Column 18,
Line 64, "11 a-α-cDNA" should read --11a-α-cDNA--.

Column 59,
Line 59, "a-GDH or 13 -GDH" should read --α-GDH or β-GDH--.

Signed and Sealed this

Twenty-eighth Day of July, 2009

JOHN DOLL
*Acting Director of the United States Patent and Trademark Office*